US011166735B2

(12) United States Patent
Cherry et al.

(10) Patent No.: US 11,166,735 B2
(45) Date of Patent: Nov. 9, 2021

(54) RETRIEVAL DEVICE

(71) Applicant: United States Endoscopy Group, Inc., Mentor, OH (US)

(72) Inventors: Terra Cherry, Mentor, OH (US); Aaron Boyce, Eastlake, OH (US); Christopher J. Kaye, Concord, OH (US); Cynthia Ann Ranallo, Eastlake, OH (US); Alex Uspenski, Rock Creek, OH (US)

(73) Assignee: United States Endoscopy Group, Inc., Mentor, OH (US)

( * ) Notice: Subject to any disclaimer, the term of this patent is extended or adjusted under 35 U.S.C. 154(b) by 0 days.

(21) Appl. No.: 14/875,028

(22) Filed: Oct. 5, 2015

(65) Prior Publication Data
US 2016/0045210 A1 Feb. 18, 2016

Related U.S. Application Data

(63) Continuation of application No. 14/061,395, filed on Oct. 23, 2013, now Pat. No. 9,204,888, which is a
(Continued)

(51) Int. Cl.
*A61B 17/221* (2006.01)
*A61B 17/00* (2006.01)
*A61B 17/22* (2006.01)

(52) U.S. Cl.
CPC ...... *A61B 17/221* (2013.01); *A61B 17/00234* (2013.01); *A61B 2017/0034* (2013.01);
(Continued)

(58) Field of Classification Search
CPC ............ A61B 17/221; A61B 17/00234; A61B 2017/00287; A61B 2017/22035; A61B 2017/2212
See application file for complete search history.

(56) References Cited

U.S. PATENT DOCUMENTS 460,940 A 10/1891 Baugh
2,197,921 A 4/1940 Brown
(Continued)

FOREIGN PATENT DOCUMENTS

DE 19938902 A1 4/2000
EP 0446020 A1 9/1991
(Continued)

OTHER PUBLICATIONS

English Translation of Office Action from Japanese Patent Application No. 2016-052587 dated Jan. 31, 2017.
(Continued)

*Primary Examiner* — Diane D Yabut
*Assistant Examiner* — Christian D Knauss
(74) *Attorney, Agent, or Firm* — Calfee, Hlater & Griswold LLP

(57) ABSTRACT

An endoscopic device for retrieving an object from within a human body is disclosed. The device includes a support assembly, a transmitting assembly, a wire, and a net element. The support assembly has a base and a tubular member. The transmitting assembly includes a handle and a motion transmitting link fixed to the handle and extending through at least a portion of the tubular member. The wire defines a loop portion and two leg portions. A proximal end of each leg portion is secured to the link by a first connection and the two leg portions are secured to each other by at least a second connection distal from the first connection. The net element has a distally protruding portion secured to the loop portion and a proximally protruding portion secured relative to the leg portions.

10 Claims, 10 Drawing Sheets

Related U.S. Application Data continuation of application No. 13/213,689, filed on Aug. 19, 2011, now Pat. No. 8,591,521, which is a continuation-in-part of application No. 12/135,473, filed on Jun. 9, 2008, now Pat. No. 8,016,838.

(60) Provisional application No. 60/942,788, filed on Jun. 8, 2007.

(52) U.S. Cl.
CPC .............. *A61B 2017/00287* (2013.01); *A61B 2017/00367* (2013.01); *A61B 2017/00438* (2013.01); *A61B 2017/2212* (2013.01); *A61B 2017/22035* (2013.01)

(56) References Cited

U.S. PATENT DOCUMENTS

| | | | |
|---|---|---|---|
| 2,626,447 A | 1/1953 | Hunt | |
| 3,805,791 A | 4/1974 | Seuberth et al. | |
| 4,083,706 A | 4/1978 | Wiley | |
| 4,146,019 A | 3/1979 | Bass et al. | |
| 4,200,104 A | 4/1980 | Harris | |
| 4,202,338 A | 5/1980 | Bitrolf | |
| 4,256,113 A | 3/1981 | Chamness | |
| 4,311,143 A | 1/1982 | Komlya | |
| 4,493,320 A | 1/1985 | Treat | |
| 4,905,691 A | 3/1990 | Rydell | |
| 4,966,589 A | 10/1990 | Kaufman | |
| 5,009,642 A | 4/1991 | Sahi | |
| 5,057,114 A | 10/1991 | Wittich et al. | |
| 5,059,199 A | 10/1991 | Okada et al. | |
| 5,078,716 A | 1/1992 | Doll | |
| 5,084,054 A | 1/1992 | Bencini et al. | |
| 5,098,441 A | 3/1992 | Wechler | |
| 5,122,147 A | 6/1992 | Sewell, Jr. | |
| 5,123,906 A | 6/1992 | Kelman | |
| 5,147,371 A | 9/1992 | Washington | |
| 5,156,590 A | 10/1992 | Vilmar | |
| 5,171,233 A | 12/1992 | Amplatz et al. | |
| 5,190,542 A | 3/1993 | Nakao | |
| 5,192,280 A | 3/1993 | Parins | |
| 5,192,286 A | 3/1993 | Phan et al. | |
| 5,201,740 A | 4/1993 | Nakao et al. | |
| 5,207,686 A | 5/1993 | Dolgin | |
| 5,279,548 A | 1/1994 | Essig et al. | |
| 5,336,227 A | 8/1994 | Nakao et al. | |
| 5,354,303 A | 10/1994 | Spaeth et al. | |
| 5,373,854 A | 12/1994 | Kolozsi | |
| 5,374,273 A | 12/1994 | Nakao et al. | |
| 5,376,094 A | 12/1994 | Kline | |
| 5,417,697 A | 5/1995 | Wilk et al. | |
| 5,423,830 A | 6/1995 | Schneebaum et al. | |
| 5,441,503 A | 8/1995 | Considine et al. | |
| 5,449,372 A | 9/1995 | Schmaitz et al. | |
| 5,480,404 A | 1/1996 | Kammerer et al. | |
| 5,496,330 A | 3/1996 | Bates et al. | |
| 5,501,692 A | 3/1996 | Riza | |
| 5,536,248 A | 7/1996 | Weaver et al. | |
| 5,542,948 A | 8/1996 | Weaver et al. | |
| 5,599,299 A | 2/1997 | Weaver et al. | |
| 5,599,300 A | 2/1997 | Weaver et al. | |
| 5,643,283 A | 7/1997 | Younker | |
| 5,666,970 A | 9/1997 | Smith | |
| 5,741,271 A | 4/1998 | Nakao et al. | |
| 5,759,187 A | 6/1998 | Nakao et al. | |
| 5,779,686 A | 7/1998 | Sato et al. | |
| 5,782,840 A | 7/1998 | Nakao et al. | |
| 5,785,689 A | 7/1998 | Alvarez | |
| 5,788,681 A | 8/1998 | Weaver et al. | |
| 5,810,776 A | 9/1998 | Bacich et al. | |
| 5,843,028 A | 12/1998 | Weaver et al. | |
| 5,843,051 A | 12/1998 | Adams et al. | |
| 5,846,248 A | 12/1998 | Chu et al. | |
| 5,860,987 A | 1/1999 | Ratcliff et al. | |
| 5,906,594 A | 5/1999 | Scarfone et al. | |
| 5,906,621 A | 5/1999 | Secrest et al. | |
| 5,947,979 A | 9/1999 | Ouchi et al. | |
| 5,961,526 A | 10/1999 | Chu et al. | |
| 5,964,740 A | 10/1999 | Ouchi et al. | |
| 5,971,994 A | 10/1999 | Fritzsch | |
| 5,971,995 A | 10/1999 | Rousseau | |
| 5,976,073 A | 11/1999 | Ouchi | |
| 5,989,264 A | 11/1999 | Wright | |
| 5,997,547 A | 12/1999 | Nakao et al. | |
| 6,007,546 A | 12/1999 | Snow et al. | |
| 6,010,512 A | 1/2000 | Chu et al. | |
| 6,015,391 A | 1/2000 | Rishton et al. | |
| 6,015,415 A * | 1/2000 | Avellanet ............... | A61B 18/14 606/110 |
| 6,050,995 A | 4/2000 | Durgin | |
| 6,068,603 A | 5/2000 | Suzuki | |
| 6,093,195 A | 7/2000 | Ouchi | |
| 6,123,665 A | 9/2000 | Kawano | |
| 6,142,956 A | 11/2000 | Kortenbach et al. | |
| 6,171,315 B1 | 1/2001 | Chu et al. | |
| 6,174,291 B1 | 1/2001 | McMahon et al. | |
| 6,183,482 B1 | 2/2001 | Bates et al. | |
| 6,190,353 B1 | 2/2001 | Makower et al. | |
| 6,193,672 B1 | 2/2001 | Clement | |
| 6,210,416 B1 | 4/2001 | Chu et al. | |
| 6,224,611 B1 | 5/2001 | Ouchi | |
| 6,235,026 B1 | 5/2001 | Smith | |
| 6,245,078 B1 | 6/2001 | Ouchi | |
| 6,264,664 B1 | 7/2001 | Avellanet | |
| 6,299,612 B1 | 10/2001 | Ouchi | |
| 6,315,782 B1 | 11/2001 | Chu et al. | |
| 6,319,260 B1 | 11/2001 | Yamamoto | |
| 6,352,503 B1 | 3/2002 | Matsui et al. | |
| 6,375,661 B2 | 4/2002 | Chu et al. | |
| 6,383,194 B1 | 5/2002 | Pothula | |
| 6,383,198 B1 | 5/2002 | Hamilton | |
| 6,407,333 B1 | 6/2002 | Schroen | |
| 6,409,733 B1 | 6/2002 | Conlon et al. | |
| 6,440,138 B1 | 8/2002 | Reiley et al. | |
| 6,458,074 B1 | 10/2002 | Matsui et al. | |
| 6,500,182 B2 | 12/2002 | Foster | |
| 6,517,551 B1 | 2/2003 | Driskill | |
| 6,527,753 B2 | 3/2003 | Sekine et al. | |
| 6,527,781 B2 | 3/2003 | Bates et al. | |
| 6,602,262 B2 | 8/2003 | Griego et al. | |
| 6,616,654 B2 | 9/2003 | Mollenauer | |
| 6,616,659 B1 | 9/2003 | de la Torre et al. | |
| 6,669,716 B1 | 12/2003 | Gilson et al. | |
| 6,685,722 B1 | 2/2004 | Rosenbluth et al. | |
| 6,730,097 B2 | 5/2004 | Dennis | |
| 6,743,228 B2 | 6/2004 | Lee et al. | |
| 6,770,066 B1 | 8/2004 | Weaver et al. | |
| 6,773,432 B1 | 8/2004 | Clayman et al. | |
| 6,814,739 B2 | 11/2004 | Secrest | |
| 6,827,710 B1 | 12/2004 | Money et al. | |
| 6,945,956 B2 | 9/2005 | Waldhauser et al. | |
| 7,001,354 B2 | 2/2006 | Suzuki et al. | |
| 7,037,291 B2 | 5/2006 | Lee et al. | |
| 7,037,307 B2 | 5/2006 | Dennis | |
| 7,041,116 B2 | 5/2006 | Goto et al. | |
| 7,044,947 B2 | 5/2006 | de la Torre et al. | |
| 7,104,990 B2 | 9/2006 | Jenkins et al. | |
| 7,122,003 B2 | 10/2006 | Nakao | |
| 7,147,635 B2 | 12/2006 | Ciarrocca | |
| 7,270,663 B2 | 9/2007 | Nakao | |
| 7,387,632 B2 | 6/2008 | Ouchi | |
| 7,547,310 B2 | 6/2009 | Whitfield | |
| 7,575,585 B2 | 8/2009 | Goto et al. | |
| 7,632,294 B2 | 12/2009 | Milbodker et al. | |
| 7,691,110 B2 | 4/2010 | Secrest et al. | |
| 7,704,249 B2 | 4/2010 | Woloszko et al. | |
| 7,758,591 B2 | 7/2010 | Griego et al. | |
| 7,785,250 B2 | 8/2010 | Nakao | |
| 7,951,073 B2 | 5/2011 | Freed | |
| 7,972,265 B1 | 7/2011 | Chin et al. | |
| 8,016,838 B2 | 9/2011 | Kaye | |
| 8,057,484 B2 | 11/2011 | Secrest | |
| 8,066,689 B2 | 11/2011 | Mitelberg et al. | |

(56) References Cited

U.S. PATENT DOCUMENTS

| | | |
|---|---|---|
| 8,070,756 B2 | 12/2011 | Secrest |
| 8,075,572 B2 | 12/2011 | Stefanchik et al. |
| 8,100,905 B2 | 1/2012 | Weitzner |
| 8,114,099 B2 | 2/2012 | Shipp |
| 8,128,592 B2 | 3/2012 | Mitelberg et al. |
| 8,167,893 B2 | 5/2012 | Motosugi |
| 8,187,266 B2 | 5/2012 | Dickens et al. |
| 8,216,272 B2 | 7/2012 | Shipp |
| 8,241,210 B2 | 8/2012 | Lunsford et al. |
| 8,267,933 B2 | 9/2012 | Hamou |
| 8,282,658 B2 | 10/2012 | Knapp et al. |
| 8,298,243 B2 | 10/2012 | Carlton et al. |
| 8,317,771 B2 | 11/2012 | Mitelberg et al. |
| 8,328,803 B2 | 12/2012 | Regadas |
| 8,343,168 B2 | 1/2013 | Kaye et al. |
| 8,357,148 B2 | 1/2013 | Boulais et al. |
| 8,366,612 B2 | 2/2013 | Rosenthal |
| 8,372,066 B2 | 2/2013 | Manwaring et al. |
| 8,388,630 B2 | 3/2013 | Teague et al. |
| 8,591,521 B2 | 11/2013 | Cherry et al. |
| 9,486,188 B2 | 11/2016 | Secrest et al. |
| 9,572,591 B2 | 2/2017 | Haack |
| 9,730,716 B2 | 8/2017 | Secrest |
| 9,872,700 B2 | 1/2018 | Haack |
| 2002/0049423 A1 | 4/2002 | Howell et al. |
| 2002/0091394 A1 | 7/2002 | Reynolds et al. |
| 2002/0151889 A1 | 10/2002 | Swanson et al. |
| 2003/0004538 A1 | 1/2003 | Secrest et al. |
| 2003/0139750 A1 | 7/2003 | Shinozuka et al. |
| 2003/0195470 A1 | 10/2003 | Ponzi |
| 2003/0195492 A1 | 10/2003 | Gobron et al. |
| 2003/0216753 A1 | 11/2003 | Nishtala et al. |
| 2003/0236519 A1 | 12/2003 | Kear |
| 2004/0059352 A1 | 3/2004 | Burbank et al. |
| 2004/0092953 A1 | 5/2004 | Salameth |
| 2004/0158127 A1 | 8/2004 | Okada |
| 2005/0043743 A1 | 2/2005 | Dennis |
| 2005/0085808 A1 | 4/2005 | Nakao |
| 2005/0101987 A1* | 5/2005 | Salahieh ............... A61F 2/013 606/200 |
| 2005/0107668 A1 | 5/2005 | Smith |
| 2005/0165412 A1 | 7/2005 | Secrest et al. |
| 2005/0267489 A1 | 12/2005 | Secrest et al. |
| 2005/0267490 A1 | 12/2005 | Secrest et al. |
| 2006/0009759 A1 | 1/2006 | Christian et al. |
| 2006/0058776 A1 | 3/2006 | Bilsbury |
| 2006/0229640 A1 | 10/2006 | Whitfield |
| 2006/0235433 A1 | 10/2006 | Secrest |
| 2006/0247662 A1* | 11/2006 | Schwartz ............ A61B 17/221 606/114 |
| 2006/0264977 A1 | 11/2006 | Dana et al. |
| 2007/0016224 A1* | 1/2007 | Nakao ................ A61B 17/221 606/113 |
| 2007/0016225 A1 | 1/2007 | Nakao |
| 2007/0250070 A1 | 10/2007 | Nobis et al. |
| 2007/0288035 A1 | 12/2007 | Okada |
| 2008/0045945 A1 | 2/2008 | Hamou |
| 2008/0183184 A1 | 7/2008 | Kaye et al. |
| 2008/0306336 A1 | 12/2008 | Kaye |
| 2009/0043317 A1 | 2/2009 | Cavanaugh et al. |
| 2009/0112244 A1 | 4/2009 | Freudenthal |
| 2010/0036375 A1 | 2/2010 | Regadas |
| 2010/0268206 A1 | 10/2010 | Manwaring et al. |
| 2010/0268216 A1 | 10/2010 | Manwaring |
| 2011/0106077 A1 | 5/2011 | Yanuma et al. |
| 2011/0106107 A1 | 5/2011 | Binmoeller et al. |
| 2012/0004666 A1 | 1/2012 | Cowley et al. |
| 2012/0046667 A1 | 2/2012 | Cherry |
| 2012/0172662 A1 | 7/2012 | Kappel et al. |
| 2012/0172864 A1 | 7/2012 | Farin et al. |
| 2012/0184967 A1 | 7/2012 | Saleh |
| 2012/0283723 A1 | 11/2012 | Jenkins et al. |
| 2013/0018384 A1 | 1/2013 | Kappel et al. |
| 2013/0018385 A1 | 1/2013 | Keene et al. |
| 2014/0243885 A1 | 8/2014 | Eckhouse et al. |
| 2014/0276810 A1 | 9/2014 | Raybin |
| 2014/0276911 A1 | 9/2014 | Smith et al. |
| 2015/0066045 A1 | 3/2015 | Haack et al. |
| 2015/0105789 A1 | 4/2015 | Raybin et al. |
| 2015/0157345 A1 | 6/2015 | Haack et al. |
| 2016/0045210 A1 | 2/2016 | Cherry et al. |
| 2016/0242804 A1 | 8/2016 | Fleury |
| 2017/0007277 A1 | 1/2017 | Drapeau |
| 2017/0049471 A1 | 2/2017 | Gaffney |
| 2017/0231647 A1 | 8/2017 | Saunders |
| 2018/0028220 A1 | 2/2018 | Smith et al. |

FOREIGN PATENT DOCUMENTS

| | | |
|---|---|---|
| EP | 463363 A2 | 1/1992 |
| EP | 758551 A1 | 2/1997 |
| EP | 1180349 A1 | 2/2002 |
| EP | 1870015 A1 | 12/2007 |
| JP | 354652 | 5/1991 |
| JP | 5091686 | 4/1993 |
| JP | 3250621 | 8/1993 |
| JP | H06154161 A | 6/1994 |
| JP | H07101802 A1 | 4/1995 |
| JP | 10071166 | 3/1998 |
| JP | 10174688 | 6/1998 |
| JP | 11047154 | 2/1999 |
| JP | 11226024 | 8/1999 |
| JP | H11309150 A | 11/1999 |
| JP | 2000175930 | 6/2000 |
| JP | 2000210295 | 8/2000 |
| JP | 2000316868 | 11/2000 |
| JP | 2000342600 | 12/2000 |
| JP | 2003052707 | 2/2003 |
| JP | 2003511140 | 3/2003 |
| JP | 2004-532683 A | 10/2004 |
| JP | 2007534451 | 11/2007 |
| WO | 93015671 A1 | 8/1993 |
| WO | 9942041 A1 | 8/1999 |
| WO | 9951159 A1 | 10/1999 |
| WO | 02094082 A2 | 11/2002 |
| WO | 03105674 A2 | 12/2003 |
| WO | 05115116 A2 | 12/2005 |
| WO | 05115120 A2 | 12/2005 |
| WO | 2006112231 A1 | 10/2006 |
| WO | 2007000452 A2 | 1/2007 |
| WO | 2008044615 A1 | 4/2008 |
| WO | 08094931 A2 | 8/2008 |
| WO | 08154406 A1 | 12/2008 |

OTHER PUBLICATIONS

International Search Report and Written Opinion from PCT/US2014/053828 dated Dec. 30, 2014.
International Preliminary Examination Report from PCT/US02/15465 dated Nov. 12, 2003.
International Search Report from PCT/US05/18294 dated May 25, 2005, 10 pages.
International Search Report and Written Opinion from PCT/US05/18497 dated May 8, 2008.
Interntional Search Report and Written Opinion from PCT/US08/52342 dated Jul. 30, 2008.
International Search Report and Written Opinion from PCT/US08/066161 dated Sep. 22, 2008.
International Search Report and Written Opinion from PCT/US2014/053828 dated Dec. 20, 2014.
Office Action from U.S. Appl. No. 10/146,273 dated Oct. 22, 2003.
Response from U.S. Appl. No. 10/146,273 dated Jan. 16, 2004.
Office Action from U.S. Appl. No. 10/146,273 dated Apr. 14, 2004.
Response from U.S. Appl. No. 10/146,273 dated May 26, 2004.
Notice of Allowance from U.S. Appl. No. 10/146,273 dated Jul. 12, 2004.
Office Action from U.S. Appl. No. 10/965,542 dated Jun. 25, 2008.
Interview Summary from U.S. Appl. No. 10/965,542 dated Oct. 14, 2008.
Response from U.S. Appl. No. 10/965,542 dated Oct. 27, 2008.
Office Action from U.S. Appl. No. 10/965,542 dated Feb. 4, 2009.

(56) References Cited

OTHER PUBLICATIONS

Response from U.S. Appl. No. 10/965,542 dated Aug. 4, 2009.
Office Action from U.S. Appl. No. 10/965,542 dated Oct. 14, 2009.
Response from U.S. Appl. No. 10/965,542 dated Apr. 14, 2010.
Office Action from U.S. Appl. No. 10/965,542 dated Jun. 30, 2010.
Response from U.S. Appl. No. 10/965,542 dated Dec. 29, 2010.
Office Action from U.S. Appl. No. 10/965,542 dated May 21, 2013.
Response from U.S. Appl. No. 10/965,542 dated Sep. 23, 2013.
Office Action from U.S. Appl. No. 10/965,542 dated Dec. 27, 2013.
RCE and Response to Office Action from U.S. Appl. No. 10/965,542 dated May 27, 2014.
Office Action from U.S. Appl. No. 10/965,542 dated Aug. 11, 2014.
Interview Summary from U.S. Appl. No. 10/965,542 dated Dec. 17, 2014.
Amendment from U.S. Appl. No. 10/965,542 dated Jan. 12, 2015.
Office Action from U.S. Appl. No. 10/965,542 dated Feb. 20, 2015.
Response to Office Action from U.S. Appl. No. 10/965,542 dated Aug. 20, 2015.
Office Action from U.S. Appl. No. 10/965,542 dated Sep. 18, 2015.
Office Action from U.S. Appl. No. 11/137,763 dated Jun. 24, 2009.
Supplemental Office Action from U.S. Appl. No. 11/137,763 dated Sep. 9, 2009.
Response from U.S. Appl. No. 11/137,763 dated Mar. 3, 2010.
Office Action from U.S. Appl. No. 11/137,763 dated May 25, 2010.
Response from U.S. Appl. No. 11/137,763 dated Jul. 23, 2010.
Advisory Action from U.S. Appl. No. 11/137,763 dated Aug. 5, 2010.
Office Action from U.S. Appl. No. 11/137,763 dated Dec. 23, 2010.
Interview Summary from U.S. Appl. No. 11/137,763 dated May 12, 2011.
Response from U.S. Appl. No. 11/137,763 dated May 23, 2011.
Office Action from U.S. Appl. No. 11/137,763 dated Aug. 4, 2011.
Response from U.S. Appl. No. 11/137,763 dated Aug. 22, 2011.
Notice of Allowance from U.S. Appl. No. 11/137,763 dated Sep. 19, 2011.
Office Action from U.S. Appl. No. 11/137,814 dated May 16, 2007.
Response from U.S. Appl. No. 11/137,814 dated Aug. 16, 2007.
Office Action from U.S. Appl. No. 11/137,814 dated Dec. 7, 2007.
Response from U.S. Appl. No. 11/137,814 dated Apr. 7, 2008.
Office Action from U.S. Appl. No. 11/137,814 dated Jul. 18, 2008.
Response from U.S. Appl. No. 11/137,814 dated Sep. 18, 2008.
Interview Summary and Advisory Action from U.S. Appl. No. 11/137,814 dated Oct. 14, 2008.
Response from U.S. Appl. No. 11/137,814 dated Nov. 18, 2008.
Office Action from U.S. Appl. No. 11/137,814 dated Feb. 12, 2009.
Response from U.S. Appl. No. 11/137,814 dated Aug. 12, 2009.
Office Action from U.S. Appl. No. 11/137,814 dated Nov. 23, 2009.
Response from U.S. Appl. No. 11/137,814 dated Jan. 19, 2010.
Notice of Allowance from U.S. Appl. No. 11/137,814 dated Feb. 18, 2010.
Office Action from U.S. Appl. No. 11/404,345 dated Jun. 27, 2008.
Interview Summary from U.S. Appl. No. 11/404,345 dated Oct. 7, 2008.
Response from U.S. Appl. No. 11/404,345 dated Nov. 26, 2008.
Office Action from U.S. Appl. No. 11/404,345 dated Mar. 11, 2010.
Response from U.S. Appl. No. 11/404,345 dated May 11, 2010.
Advisory Action from U.S. Appl. No. 11/404,345 dated May 27, 2010.
Response from U.S. Appl. No. 11/404,345 dated Sep. 13, 2010.
Office Action from U.S. Appl. No. 11/404,345 dated Dec. 29, 2010.
Response from U.S. Appl. No. 11/404,345 dated May 25, 2011.
Notice of Allowance from U.S. Appl. No. 11/404,345 dated Aug. 19, 2011.
Office Action from U.S. Appl. No. 12/021,903 dated Dec. 10, 2009.
Response from U.S. Appl. No. 12/021,903 dated Jun. 9, 2010.
Office Action from U.S. Appl. No. 12/021,903 dated Aug. 5, 2010.
Response from U.S. Appl. No. 12/021,903 dated Oct. 7, 2010.
Interview Summary from U.S. Appl. No. 12/021,903 dated Oct. 5, 2010.
Offce Action from U.S. Appl. No. 12/021,903 dated Dec. 29, 2011.
Interview Summary from U.S. Appl. No. 12/021,903 dated Mar. 21, 2012.
Response from U.S. Appl. No. 12/021,903 dated May 25, 2012.
Notice of Allowance from U.S. Appl. No. 12/021,903 dated Aug. 9, 2012.
Notice of Allowance from U.S. Appl. No. 12/021,903 dated Nov. 20, 2012.
Office action from U.S. Appl. No. 12/135,473 dated Nov. 16, 2010.
Response from U.S. Appl. No. 12/135,473 dated Feb. 15, 2011.
Interview Summary from U.S. Appl. No. 12/135,473 dated Feb. 15, 2011.
Office Communication from U.S. Appl. No. 12/135,473 dated Apr. 15, 2011.
Notice of Allowance from U.S. Appl. No. 12/135,473 dated Jun. 27, 2011.
Office Action from U.S. Appl. No. 13/213,689 dated Dec. 20, 2012.
Response from U.S. Appl. No. 13/213,689 dated Mar. 18, 2013.
Notice of Allowance from U.S. Appl. No. 13/213,689 dated Jul. 23, 2013.
Office Action from U.S. Appl. No. 14/061,395 dated Jun. 18, 2015.
Response to Office Action from U.S. Appl. No. 14/061,395 dated Sep. 17, 2015.
Office Action from U.S. Appl. No. 14/016,906 dated Apr. 8, 2015.
Office Action from U.S. Appl. No. 14/565,024 dated Apr. 17, 2015.
Response to Office Action from U.S. Appl. No. 14/565,024 dated Aug. 17, 2015.
Supplemental European Search Report from European Application No. 02729222.6 dated Aug. 20, 2009.
Response from European Application No. 02729222.6 dated Nov. 17, 2009.
Office Action from European Application No. 0279222.6 dated Sep. 23, 2010.
Response from European Application No. 02729222.6 dated Jan. 28, 2011.
Office Action from European Application No. 02729222.6 dated Sep. 7, 2011.
Response from European Application No. 02729222.6 dated Jan. 10, 2012.
Search Report from European Application No. 05757183.8 dated Oct. 4, 2012.
Office Action from European Application No. 05757183.8 dated Feb. 11, 2013.
Response from European Application No. 05757183.8 dated Aug. 19, 2013.
Search Report from European Application No. 05755966.8 dated Jun. 5, 2012.
Office Action from European Application No. 05755966.8 dated Sep. 27, 2012.
Office Action from U.S. Appl. No. 14/565,024 dated Jul. 5, 2016.
Notice of Allowance from U.S. Appl. No. 14/565,024 dated Aug. 30, 2016.
Extended Search Report from European Application No. 14841802.3 dated Jan. 30, 2017.
International Search Report and Written Opinion from PCT/US02/15465 dated Aug. 26, 2013.
Response to Office Action from U.S. Appl. No. 14/016,906 dated Jul. 28, 2016.
Office Action from U.S. Appl. No. 14/016,906 dated Sep. 13, 2016.
Response to Office Action from U.S. Appl. No. 14/016,906 dated Dec. 13, 2016.
Office Action from U.S. Appl. No. 15/344,915 dated Jan. 18, 2017.
Response from European Application No. 05755966.8 dated Apr. 5, 2013.
Search Report from European Application No. 06112733.8 dated Jan. 12, 2007.
Response from European Application No. 05112733.8 dated Jan. 7, 2009.
Office Action from European Application No. 06112733.8 dated Feb. 19, 2009.
Office Action from Japanese Application No. 2007-511105 dated Sep. 3, 2009.

(56) References Cited

OTHER PUBLICATIONS

Response from Japanese Application No. 2007-511105 dated Mar. 5, 2010 along with English translation of claims and relevant portion of remarks made in Amendment.
Office Action from Japanese Application No. 2007-515282 dated Jan. 7, 2011.
Response from Japanese Application No. 2007-515282 dated Apr. 7, 2011 along with English translation of claims and relevant portion of remarks made in Amendment.
Office Action from Japanese Application No. 2007-515282 dated Jul. 27, 2011.
Response from Japanese Application No. 2007-515282 dated Mar. 5, 2012 along with relevant portion of remarks made in Amendment.
Office Action from Japanese Application No. 2009-548397 dated Sep. 28, 2012.
Response from Japanese Application No. 2009-548397 dated Mar. 28, 2013 along with English translation of claims and relevant portion of remarks made in Amendment.
Office Action from Japanese Application No. 2010-511374 dated Dec. 28, 2012.
Response from Japanese Application No. 2010-511374 dated Jul. 5, 2013 along with English translation of claims and relevant portion of remarks made in Amendment.
Advanced Lin Retrieval Devices Brochure, issued by US Endoscopy 760204, Rev. A, dated at least as early as the filing date of the subject application.
Cook Medical brochure pages, Esophageal/Gastric Colonic: Snares, 3 pgs., date is at least as early as Jul. 1, 2013.
Juan-Marie et al. Double-Lumen Snare Injector: Introducing the Double-Lumen Concept in Ancillary Pollypectomy Equipment, Gastrointestinal Endoscopy, vol. 57, No. 5, 2003.
MTW Endoskopie, brochure, one page, date is at least as early as Jul. 1, 2013.
Olympus, EndoTherapy, Polypectomy, brochure, 3 pgs., date is at least as early as Jul. 1, 2013.
English translation of Office Action in Japanese Application No. 2014-004359 dated Jan. 20, 2015.
Extended European Search Report in European Application No. 08756773.1 dated Feb. 23, 2015.
International Preliminary Report on Patentability from PCT/US2014/053828 dated Mar. 8, 2016.
Response to Office Action from U.S. Appl. No. 10/965,542 dated Jan. 19, 2016.
Notice of Allowance from U.S. Appl. No. 10/965,542 dated Jul. 11, 2016.
Response to Office Action from U.S. Appl. No. 14/016,906 dated Feb. 12, 2016.
Office Action from U.S. Appl. No. 14/016,906 dated May 31, 2016.
Response to Office Action from U.S. Appl. No. 14/565,024 dated Mar. 25, 2016.
Advisory Action from U.S. Appl. No. 14/565,024 dated Apr. 14, 2016.
Amendment from U.S. Appl. No. 14/565,024 dated Jul. 28, 2016.
Search Report from European Application No. 12162767.3 dated Dec. 23, 2015.
Office Action from U.S. Appl. No. 14/565,024 dated Dec. 9, 2015.
Office Action from European Application No. 05757183.8 dated Nov. 16, 2015.
Response to Office Action from European Application No. 05757183.8 dated Mar. 17, 2016.
Extended European Search Report in European Application No. 08714094.3 dated Jan. 27, 2016.
Response to Office Action from U.S. Appl. No. 14/016,906 dated Aug. 10, 2017.
Notice of Allowance from U.S. Appl. No. 14/016,906 dated Sep. 27, 2017.
Notice of Allowance from U.S. Appl. No. 15/344,915 dated Jun. 26, 2017.
Response to Office Action from U.S. Appl. No. 15/425,228 dated Jul. 10, 2017.
Office Action from U.S. Appl. No. 15/425,228 dated Aug. 23, 2017.
Response to Office Action from U.S. Appl. No. 15/425,228 dated Aug. 31, 2017.
Office Action from U.S. Appl. No. 14/016,906 dated Mar. 10, 2017.
Office Action from U.S. Appl. No. 15/425,228 dated Apr. 12, 2017.
Response Office Action from U.S. Appl. No. 15/344,915 dated Apr. 18, 2017.
English Translation of Office Action from Japanese Patent Application No. 2016-0540331 dated May 29, 2018.
International Search Report and Written Opinion from PCT/US18/13005 dated Mar. 29, 2018.
International Search Report and Written Opinion from PCT/US18/13017 dated Apr. 6, 2018.
Office Action from U.S. Appl. No. 15/401,545 dated Aug. 2, 2018.
Response to Office Action from U.S. Appl. No. 15/401,545 dated Oct. 30, 2018.
Communication Pursuant to Article 94(3) EPC from European Application No. 05755966.8 dated Oct. 22, 2018.
Communication Pursuant to Artile 94(3) EPC from European Application No. 12162767.3 dated Nov. 12, 2018.
Extended Search Report from European Application No. 18167984.6 dated Jul. 30, 2018.
Office Action from U.S. Appl. No. 15/401,545 dated Mar. 8, 2019.
Response to Office Action Office Action from U.S. Appl. No. 15/401,545 dated Jun. 10, 2019.
Office Action from U.S. Appl. No. 15/401,545 dated Jun. 27, 2019.
Response to Office Action Office Action from U.S. Appl. No. 15/401,545 dated Sep. 26, 2019.
Office Action from U.S. Appl. No. 15/676,725 dated Jul. 5, 2019.
Communication Pursuant to Article 94(3) from European Application No. 18167984.6 dated Jun. 6, 2019.
Response to Office Action from U.S. Appl. No. 15/676,725 dated Jan. 6, 2020.
Notice of Allowance from U.S. Appl. No. 15/401,545 dated Jan. 16, 2020.
Notice of Allowance from U.S. Appl. No. 15/866,401 dated Jan. 23, 2020.
Notice of Allowance from U.S. Appl. No. 15/676,725 dated May 14, 2020.
Notice of Allowance from U.S. Appl. No. 15/866,273 dated Jan. 23, 2020.
Notice of Allowance from U.S. Appl. No. 15/866,273 dated Apr. 22, 2020.
Notice of Allowance from U.S. Appl. No. 15/866,273 dated May 5, 2020.
Notice of Allowance from U.S. Appl. No. 15/866,273 dated Jun. 4, 2020.
Extended Search Report from European Application No. 18736126.6 dated Jul. 7, 2020.
Extended Search Report from European Application No. 20152855.1 dated Jun. 16, 2020.
Notice of Allowance from U.S. Appl. No. 15/676,725 dated Feb. 4, 2020.
Notice of Allowance from U.S. Appl. No. 15/866,401 dated Mar. 18, 2020.
Search Report from European Application No. 18736653.9 dated Oct. 12, 2020.
Communication Pursuant to Article 94(3) EPC from European Application No. 12162767.3 dated Feb. 23, 2021.
Extended Search Report from European Application 20181554.5 dated Oct. 2, 2020.

* cited by examiner

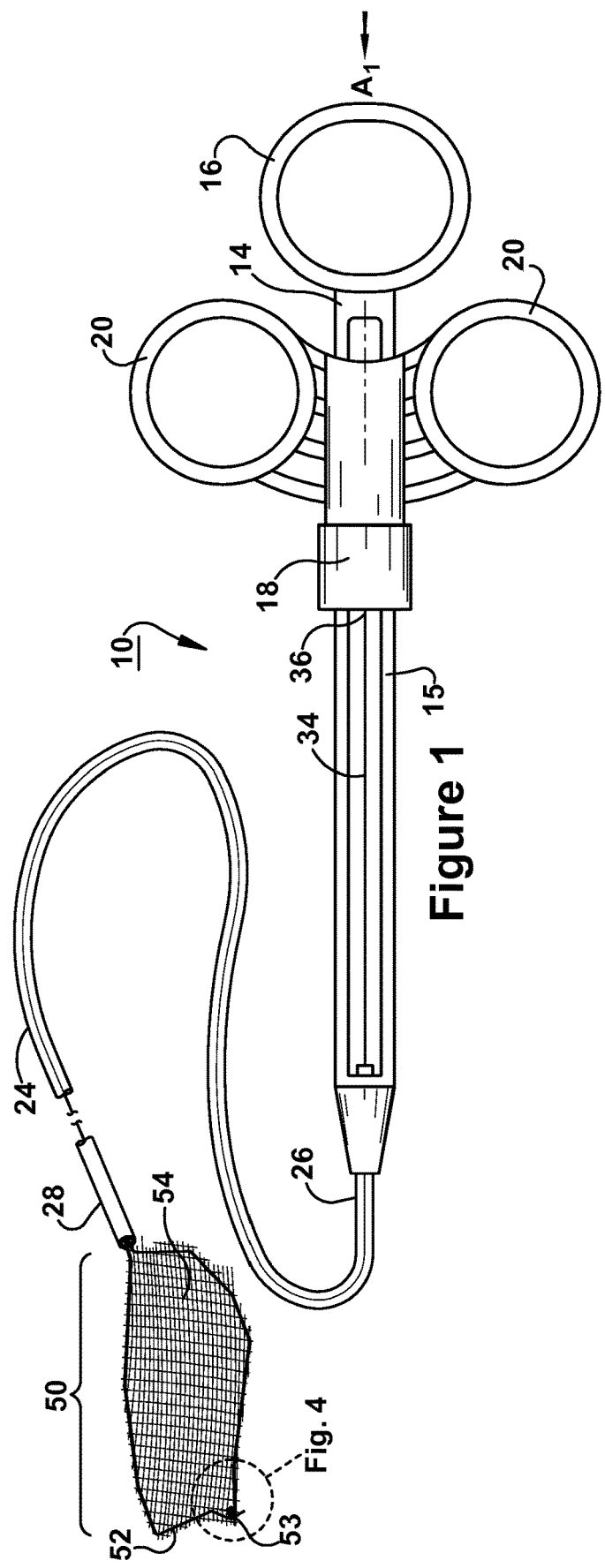
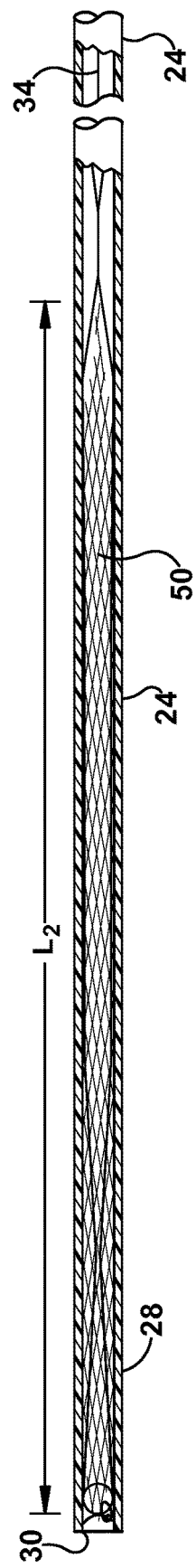
Figure 1
Figure 2

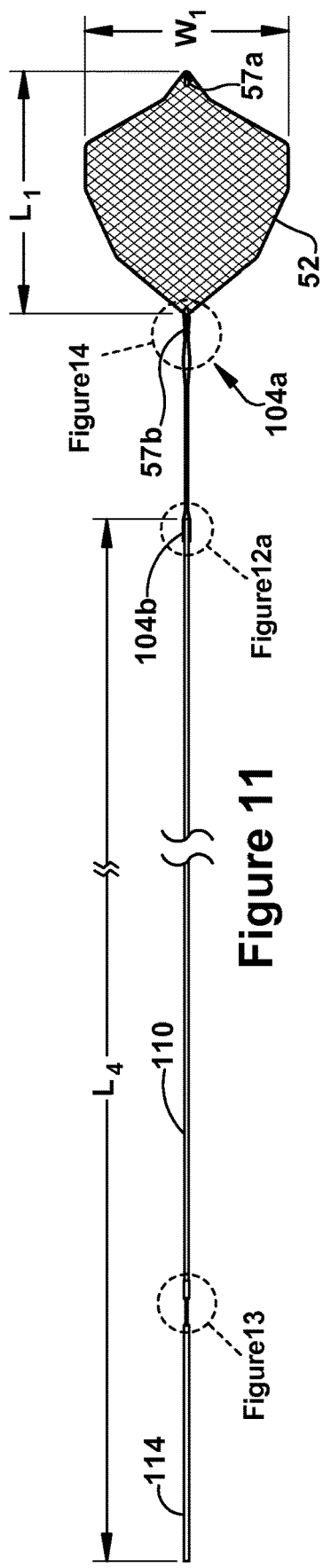
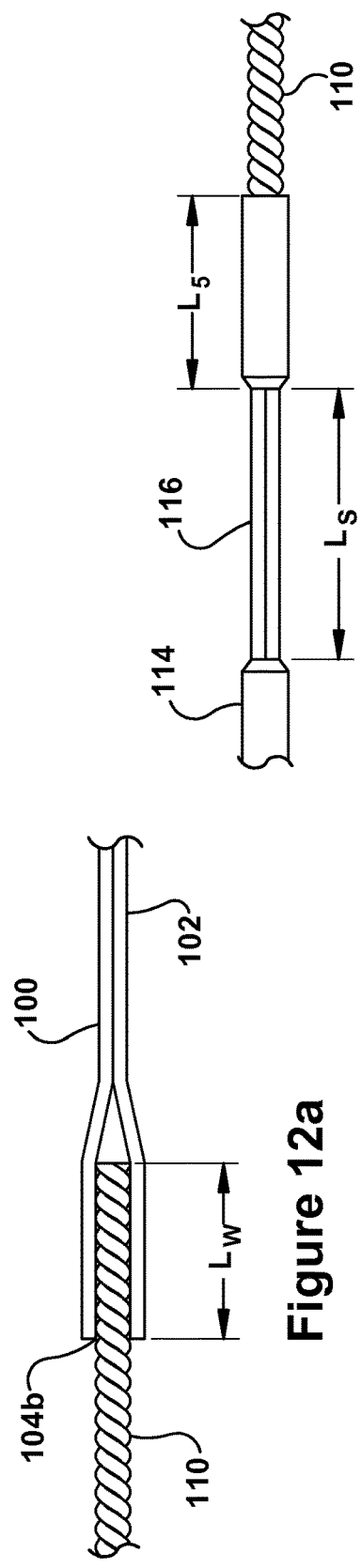
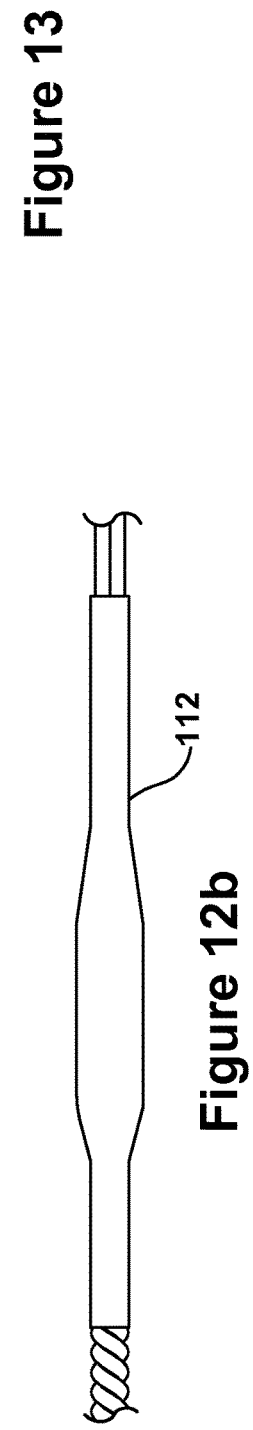
Figure 11
Figure 12a
Figure 12b
Figure 13

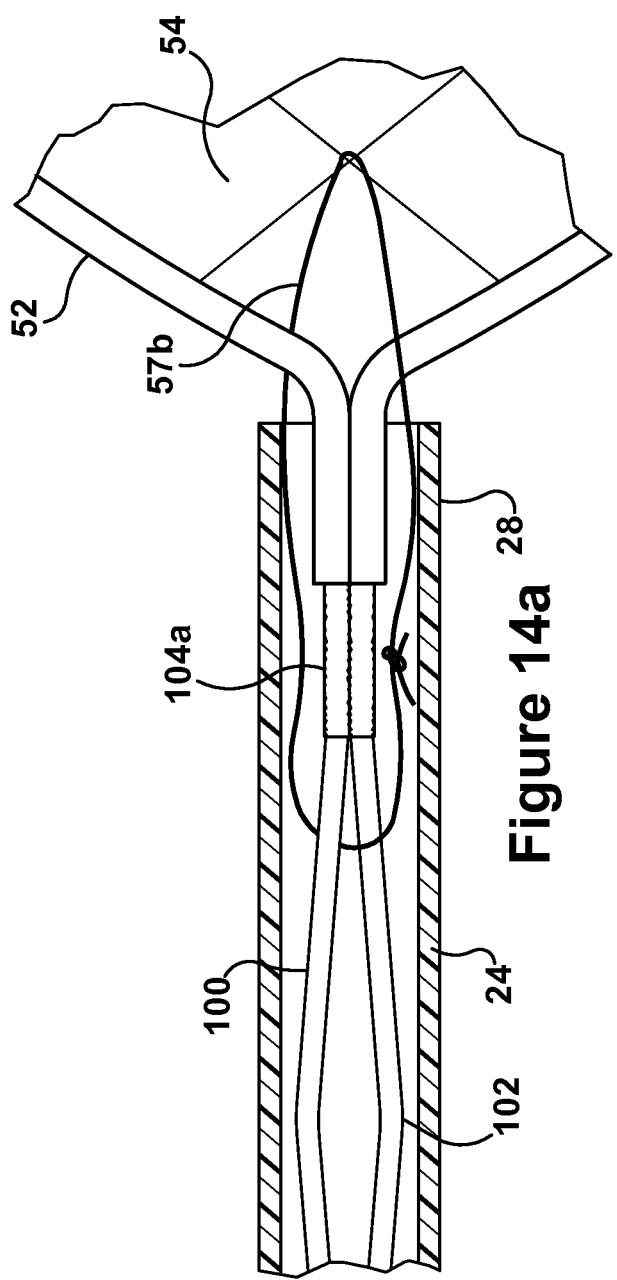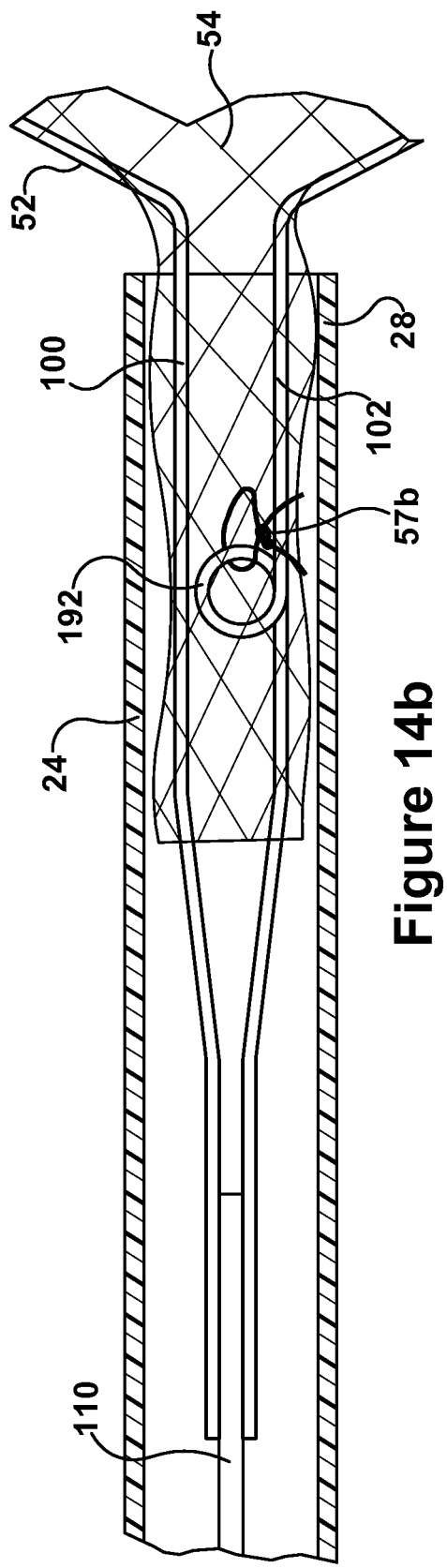

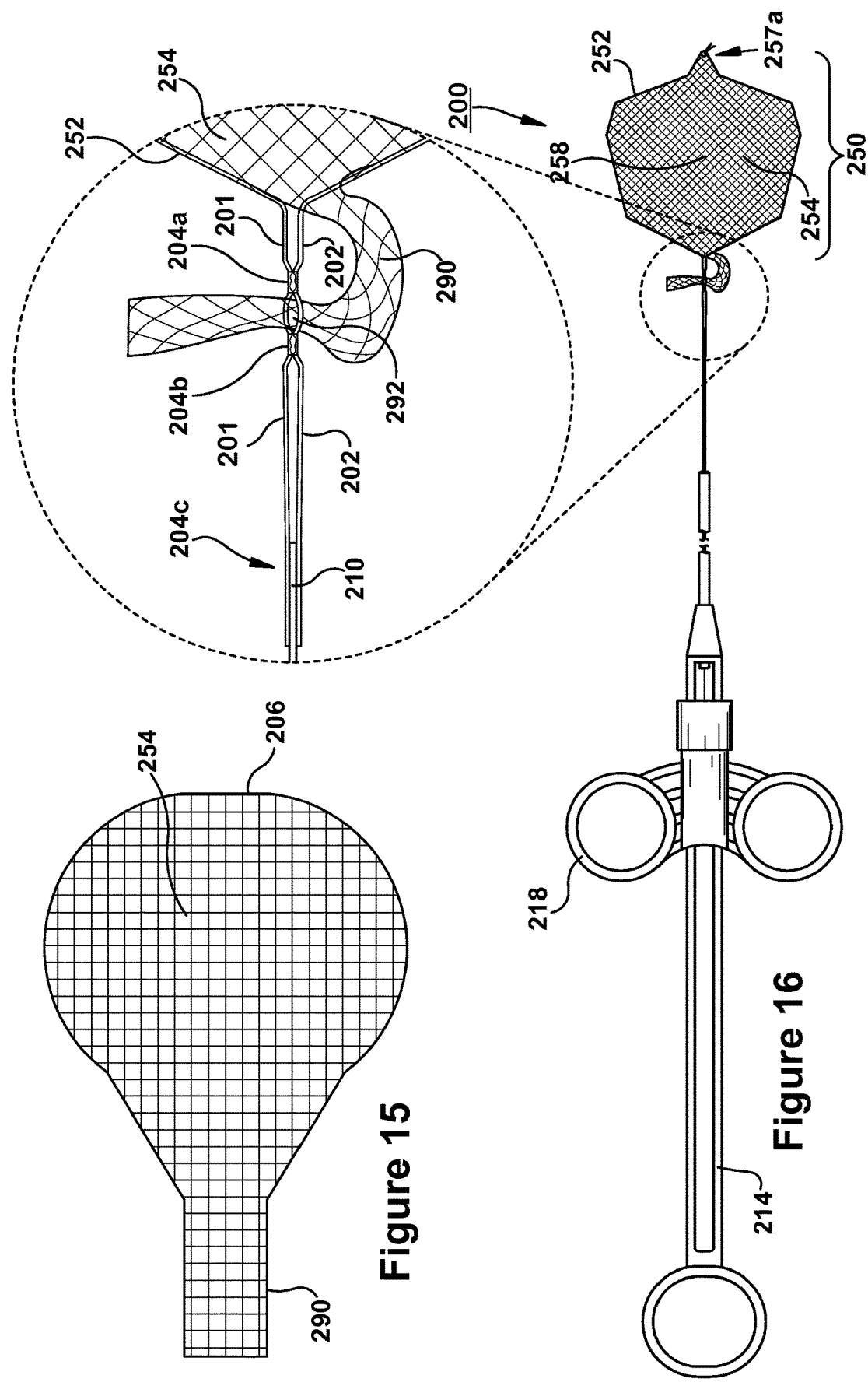

RETRIEVAL DEVICE

CROSS-REFERENCE TO RELATED APPLICATIONS

This application is a continuation of U.S. Non-Provisional patent application Ser. No. 14/061,395 entitled "Retrieval Device," filed Oct. 23, 2013, which is a continuation of U.S. Non-Provisional patent application Ser. No. 13/213,689 entitled "Retrieval Device," filed Aug. 19, 2011, and issued as U.S. Pat. No. 8,591,521 on Nov. 26, 2013, which is a continuation-in-part of U.S. Non-Provisional patent application Ser. No. 12/135,473, entitled "Retrieval Device," filed Jun. 9, 2008, and issued as U.S. Pat. No. 8,016,838 on Sep. 13, 2011, which claims priority to, and benefit of, U.S. Provisional Application No. 60/942,788, entitled "Retrieval Device," filed Jun. 8, 2007, the entire disclosures of which are incorporated herein by reference.

BACKGROUND

Endoscopic retrieval or removal devices are known in the art and are conventionally used to recover objects from inside a human subject. Such objects may include severed human tissue, foreign objects, or food bolus. Some typical devices include forceps or clasps to grab objects. Certain devices of this type are not well-suited for retrieving heavy, rounded or blunt objects such as large tissue masses, a food bolus, coins, marbles and batteries because the objects are difficult to hold secure. Further, if an object is dropped near the trachea during the removal process, the results can be catastrophic for the patient. Other devices include a variety of net support and net operating structures.

Many retrieval devices are used within an instrument channel of an endoscope during endoscopic medical procedures. These devices are generally expandable and collapsible relative to a tube inserted into the instrument channel. For example, a wire loop at the distal end of the device may expand and collapse relative to the tube by action of a handle at the proximal end of the device. Further, a net may be secured to the expandable and collapsible wire loop.

SUMMARY

In an illustrated embodiment of the invention, a device for retrieving objects, such as for example, impacted food bolus, foreign objects, and severed human tissue, is disclosed. The device is for use within an instrument channel of an endoscope during endoscopic medical procedures.

The device includes a support assembly, a transmitting assembly, a wire defining a loop portion and two leg portions, and a net element having a distally protruding portion and a proximally protruding portion. The support assembly includes a base and an elongated tubular member. The transmitting assembly includes a handle movable relative to the base, and a link having a first end fixed to the handle and a second end remote from the base. The link extends through at least a portion of the tubular member. Each leg portion is disposed proximal from the loop portion. A proximal end of each leg portion is secured to the second end of the link by a first connection. The two leg portions are secured to each other by at least a second connection at a location between the first connection and the loop portion. The distally protruding portion is secured to a distal end of the loop portion. The proximally protruding portion is secured between the two leg portions at a location proximal from the second connection.

Further features and advantages of the invention will become apparent from the following detailed description made with reference to the accompanying drawings.

BRIEF DESCRIPTION OF THE DRAWINGS

FIG. 1 is a perspective view of a retrieval device constructed in accordance with an embodiment of the present invention;

FIG. 2 is a cross-sectional fragmentary view of the distal portion of the device illustrated in FIG. 1, showing a retrieval net in a stored position within a tube;

FIG. 11 is a front elevation view of a distal portion of the device of FIG. 4;

FIGS. 12a-12b and 13 are enlarged views of the designated circular sections of FIG. 11, showing a variety of structural detail;

FIG. 14a is an enlarged sectional view of the device of FIG. 4, showing a proximal net connection;

FIG. 14b is an enlarged sectional view of the device of FIG. 4, showing another proximal net connection;

FIG. 15 is a top view of a net element according to another embodiment of the invention;

FIG. 16 is a front elevation view of a distal portion of the device according to another embodiment of the invention;

DETAILED DESCRIPTION

Figure 3:
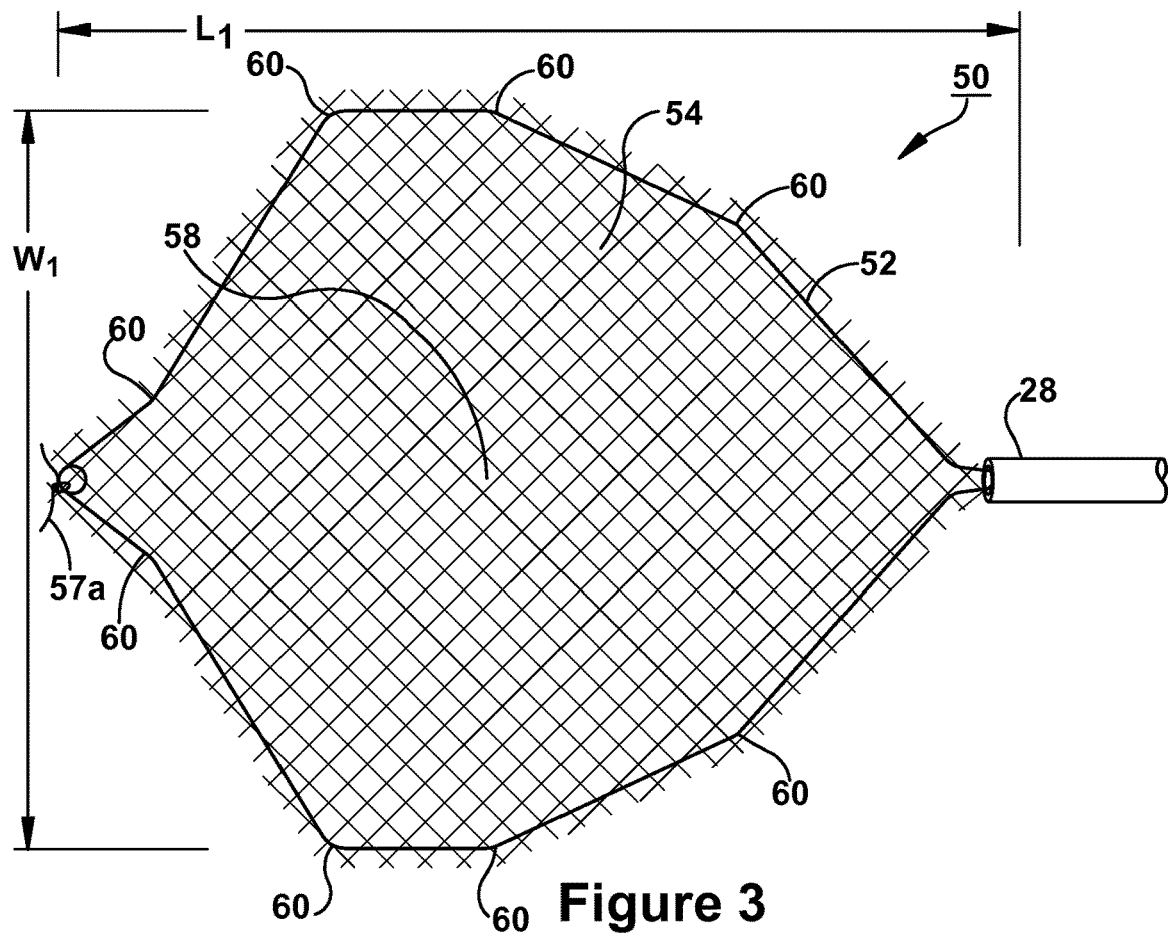
FIG. 3 is an alternative view of FIG. 2, showing the retrieval net in a deployed position outside of the tube.

The Detailed Description merely describes preferred embodiments of the invention and is not intended to limit the scope of the invention or claims in any way. Indeed, the invention as described by the claims is broader than and unlimited by the preferred embodiments, and the terms used have their full ordinary meaning.

A device for retrieving an object from within a human subject is disclosed. In discussing the device, the terms distal and proximal are used with respect to the operator's hand. In other words, when the device is used within the instrument channel of an endoscope or similar device, the proximal and distal orientation are relative to the position of the surgeon or operator of the device. Further, it should be noted that the terms first connection, second connection, third connection, and the like do not imply a manufacturing order.

It should also be noted that for the purposes of this application, the terms attach (attached), connect (connected), and link (linked) are not limited to direct attachment, connection, or linking but also include indirect attachment, connection, or linking with intermediate parts, components, or assemblies being located between the two parts being attached, connected, or linked to one another. In addition, the terms attach (attached), connect (connected), and link (linked) may include two parts integrally formed or unitarily constructed.

For exemplary purposes only, the invention will be discussed in regard to a device designed for use within an endoscope for retrieving objects within relatively tight passages, such as for example, impacted food bolus from the esophagus. It should be apparent to others with ordinary skill in the art that the discussion and Figures included in this application are by way of example only, and that the invention can be utilized with endoscopic retrieval devices having a wide variety of structures, shapes, strengths, or purposes. One of many other exemplary uses for the invention is to remove polyps from the colon.

Several exemplary devices for endoscopic retrieval of an object from within a subject are disclosed in U.S. Pat. No. 6,814,739 to Secrest et al.; application Ser. No. 10/965,542, entitled "Retrieval Device" and filed Jul. 28, 2005; and application Ser. No. 11/137,763, entitled "Retrieval Device" and filed Dec. 1, 2005, each of which incorporated herein by reference in its entirety, to the extent that any do not conflict with the present application.

As mentioned, devices using netting have been developed to capture rounded or blunt objects. In the use of devices having netting, and it is believed in the use of other devices, physicians have experienced difficulty in recovering certain objects, such as for example, impacted food bolus from the esophagus. A bolus is a mass of masticated or chewed food. In some cases, the bolus becomes impacted in the esophagus due to disease or other disorders and consequently does not pass into the stomach. It may be more difficult to position a net over an object of this type or the object may be heavier than the human tissue or foreign object for which a typical net device was originally designed. This problem is especially apparent when manipulating the device in relatively tight places within the body. As a result, netting support collapses and does not retain its shape in a deployed position when holding the captured object. Further, the netting may tear or net connections may fail causing reliability concerns.

To solve these and other problems, the retrieval device of the invention is more reliable, structurally simpler, and less costly to manufacture than prior devices. For example, in some embodiments, the proximal portion of the net element is secured to the wire that forms the loop and leg portions of the retrieval net using a shorter tether or anchor than previous designs which anchor the net element at a more proximal location. In other embodiments, no tether or anchor is used to secure the proximal portion of the net element and instead the net element is routed between welds, or other similar connections, connecting the leg portions of the wire together. Where no tether is used to secure the proximal portion of the net element, the chances of the net element breaking or tearing are reduced because the forces are distributed more evenly over a greater area instead of at an isolated point of contact.

Further, in some embodiments, the proximal portion of the net element at least partially surrounds the connection of the leg portions to the cable and/or the connection securing the leg portions together. As such, the proximal portion of the net element inhibits damage to the connections and the inside of the tubular member. The proximal portion of the net element also provides a damping effect on the cable movement toward the distal end of the tubular member when the handle is activated. This also provides more control over the deployment of the net and cable and controls the portion of the device that exits the opening of the tubular member when the retrieval net is in the deployed position. The proximal portion of the net element also helps to center the leg portions of the wire and the cable within the tubular member.

The retrieval net generally collapses and expands relative to a tube inserted through the instrument channel of the endoscope. In the collapsed position, the retrieval net is small enough in diameter to fit inside at least the distal end of a lumen of the tubing. Further, any connection securing the net element to the loop should be small enough to fit within the lumen and allow the retrieval net to collapse and expand repeatedly. The connection should also be able to hold the net element in place relative to the loop during the expansion and collapse of the retrieval net. Further, the loop is generally connected to a motion transmitting link. The motion transmitting link allows the loop to be manipulated by a handle at the proximal end of the device. As such, any connection or connections securing the loop to the motion transmitting link must also be small enough to fit within the lumen and allow the retrieval net to collapse and expand repeatedly. If either of these connections is too large, the connection may drag or catch on the inside wall of the lumen. The friction between the connection and the inside wall of the lumen may prohibit essentially a 1:1 ratio between the movement of the handle and the movement of the distal end of the loop or retrieval net.

The net element is generally supported by the loop by threading, or weaving, the flat wire through the holes in the net element. However, the net element may be supported by the loop by any suitable method known in the art. For example, the net element may wrap around the loop, like a sleeve, or be tied to the loop. Further, the net element may be secured to the wire by tethers, anchors, adhesives, or the like such that the net element is held in place relative to the loop during the expansion and collapse of the retrieval net. For example, tethers or anchors may be used to secure the net element to the distal end and the proximal end of the loop. In an embodiment of the invention, the proximal portion of the net element is attached adjacent a connection securing the two leg portions together, by a tether or anchor, such as for example, a string tie. The proximal portion of the net element may be attached using a tether or anchor to the proximal side of the connection securing the two leg portion together. The proximal portion of the net element may be attached using a tether or anchor to a 360 degree curved portion of at least one leg portion. The distal portion of the net element may also be attached using a tether or anchor to a 360 degree curved portion of the loop portion. In another embodiment, the proximal portion of the net element may be secured to the leg portions by routing the net element through connections securing the two leg portions together. The size and smooth or curved contour of these connections reduce the drag or friction on the inside wall of the lumen, permitting essentially a 1:1 ratio between the movement of the handle and the movement of the distal end of the loop or retrieval net.

Referring now to the drawings, FIG. 1 is a perspective view of a retrieval device 10 constructed in accordance with an embodiment of the invention. The device 10 includes a support base or elongated body 14. The body 14 includes a ring 16 at a proximal end. The device 10 also includes a handle 18 having two rings 20. The handle 18 is mounted over an interior section 15 of the body 14 and is movable relative to the body in the direction $A_1$ as illustrated, or in an opposing direction. For example, an operator may place a finger in each of the rings 20 and thumb of the same hand in the body ring 16. By moving the two fingers in the direction $A_1$, an operator can move the handle 18 relative to the body 14. In contrast, the handle 18 can be slid in a direction opposite $A_1$ by pulling one's fingers towards one's thumb.

The device 10 includes an elongated introducer member or tubular member 24 having a first end 26 fixed to the body 14 and a second end 28 remote from the body. The tubular member 24 and the body 14 are a fixed support assembly for the moving parts of the device 10. The tubular member 24 may be any suitable, small-diameter tube formed of a non-reactive low-friction flexible material, such as for example, polytetraflourethylene. The tubular member 24 defines a lumen with an opening 30 at the tubular member second end 28, as best seen in FIG. 2 which shows a cross-sectional view of a distal portion of the device 10.

A motion transmitting link 34 is connected to the handle 18. The link can be a solid cable, a hollow tube, or any suitable elongated object or combination of objects for transferring axial motion from the handle 18 to other parts of the device. The link 34 has a first end 36 fixed to the handle 18 and a second end remote from the body 14. As shown in the drawings, the link extends substantially through the tubular member 24 lumen. The link may be constructed of any suitable rigid material. The link may be one piece or formed from a series of pieces and connections, such as for example, hypodermic tubes, swage connections, and cables.

Still referring to FIG. 1, the device also includes a retrieval net 50. The retrieval net 50 is used by the operator to capture and retrieve objects from within a human subject. The retrieval net 50 includes a loop 52, or loop portion, and a net element 54 secured to the loop. The net element 54 is supported by the loop 52 by threading, or weaving, the loop through holes in the net element. However, the net element 54 may be supported by the loop 52 by any suitable method known in the art. Further, it should be apparent to others with ordinary skill in the art that a variety of net shapes and sizes can be utilized in the practice of this invention.

Figure 4:
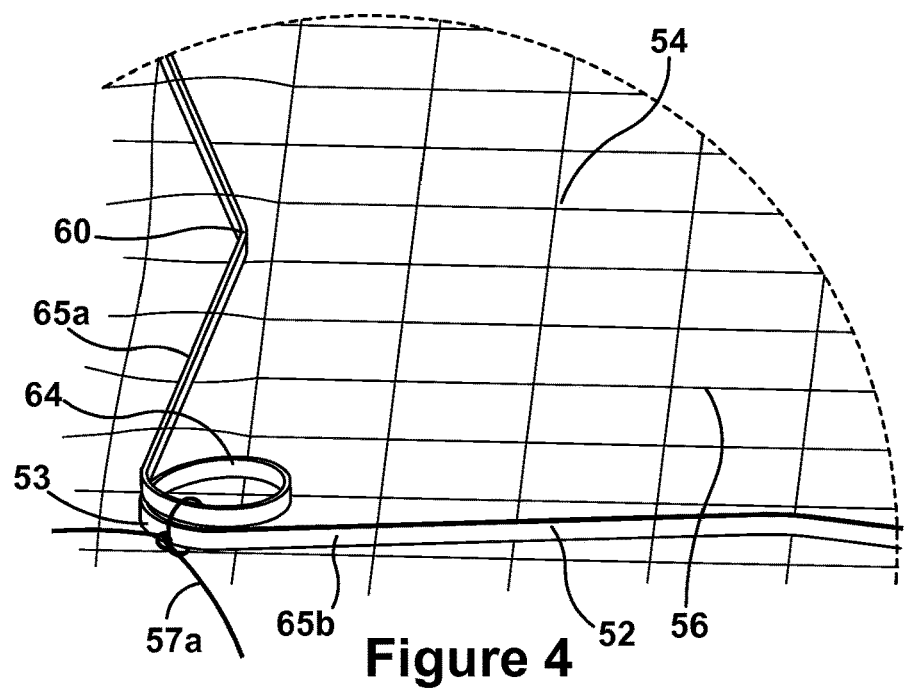
FIG. 4 is an exploded perspective view of the designated circular section of FIG. 1, showing detail of the net element and the distal end of the loop.

As shown in FIGS. 3 and 4, a tether or anchor 57a disposed at the distal portion of the net element 54 anchors the net element to the loop 52 at a distal end 53 of the loop. Other distal tether or anchor designs and distal net anchoring methods can be utilized in the practice of this invention.

As discussed, the retrieval net 50 is designed for movement between two positions. FIGS. 1 and 3 show the retrieval net 50 in a deployed position. In this position, the retrieval net 50 has a length $L_1$ and a width $W_1$. FIG. 2 is a cross-sectional view of a distal portion of the device 10, showing the retrieval net 50 in a stored position within the tube 24. In this position, the retrieval net 50 has a length $L_2$ which is considerably longer than $L_1$. As shown in FIG. 2, the retrieval net 50 is disposed within the tube 24 for deployment and retrieval through the tubular member lumen opening 30. By movement of the handle 18 relative to the body 14, the retrieval net 50 is movable between either the deployed or stored positions.

Figure 7:
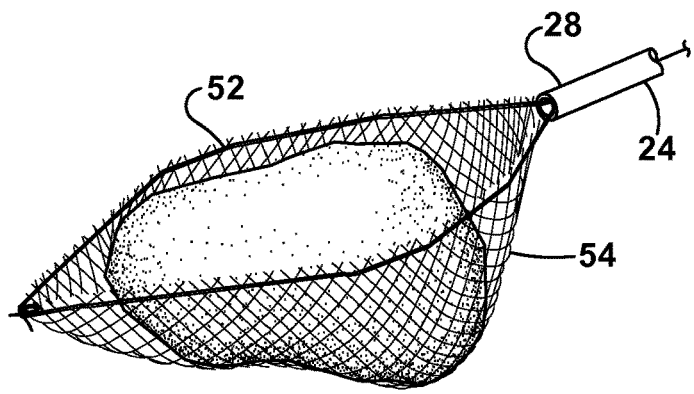
FIG. 7 is a perspective view of a distal portion of the device illustrated in FIG. 4, showing an exemplary food bolus captured within the retrieval net.

Referring again to FIG. 3, the retrieval net 50 is illustrated in a deployed position and fully expanded outside of the tube 24 second end 28. The net element 54 may be constructed of any suitable light weight material, such as for example, nylon mesh string 56, as best seen in FIG. 4. The net element 54 has a centrally located object receiving pouch section 58. To be discussed further in greater detail, captured objects rest within this section as shown in FIG. 7.

As discussed, the retrieval net 50 shown in FIG. 3 includes a loop portion 52 formed by a wire. The loop 52 acts as a support for the net element 54 when the retrieval net is deployed. The loop 52 is resiliently movable between a collapsed position shown in FIG. 2 to an expanded position shown in FIG. 3 by operator action of the handle 18 relative to the body 14. A distal end 53 of the loop 52 includes structure to resist collapse of the loop during use.

Referring now to FIG. 4, an exploded perspective view of the designated circular section of FIG. 1 is shown. In the embodiment shown, the loop 52 is formed by a flat wire constructed of a resilient material, such as for example, 304 stainless steel. The loop 52 may be constructed from a material having a tensile strength greater than 300,000 psi. Again, it should be apparent to others with ordinary skill in the art that the present invention can be utilized with a loop 52 constructed from a wide variety of materials.

The device 10 as illustrated in FIGS. 3 and 4 includes several features that promote expansion and prohibit collapse when an object is held within the net element 54 or the device is used in a relatively tight passage of the body. The loop 52 includes several collapse-resistant bends 60. The location of the bends 60 act as memory points and are retained by the loop 52 through multiple deployments. These bends 60 are constructed such that the loop 52 forms a polygon shape when deployed. As shown, the loop 52 forms a general hexagon shape. It is believed that a polygon shape is more resilient and less likely to collapse when an object is held within the net or when retrieving an object within a narrow passage. It should be understood by those with ordinary skill in the art that the polygon shape shown in FIG. 3 is for exemplary purposes only, and other polygon or non-polygon shapes can be used in the practice of the invention, such as for example oval or round shapes.

As shown in FIG. 4, the loop 52 further includes a 360 degree curved portion 64 disposed at a distal end 53 of the loop. This curved portion 64 acts as a spring tip to further prohibit collapse when an object is held within the retrieval net 50. This spring tip 64 also acts to promote polygon segments 65a, 65b to remain apart during deployment. This feature is beneficial in tight passages, such as for example, the esophagus. As mentioned, the tether or anchor 57a anchors the net element 54 to the curved portion 64 of the loop 52.

Figure 5:
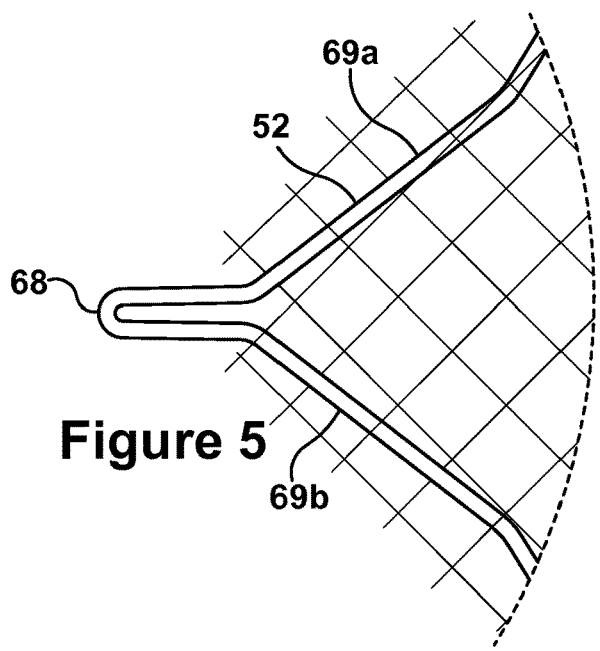
FIG. 5 is an exploded fragmentary view of the net of a retrieval device, showing an alternative distal end of the loop.

Several other embodiments include alternative shapes and structures of the distal end of the loop. FIG. 5 shows the distal end of the support wire in an alternative shape. The loop 52 is bent to form a protruding tip 68. It is believed that this shape promotes polygon segments 69a, 69b to remain apart during deployment and use.

Figure 6:
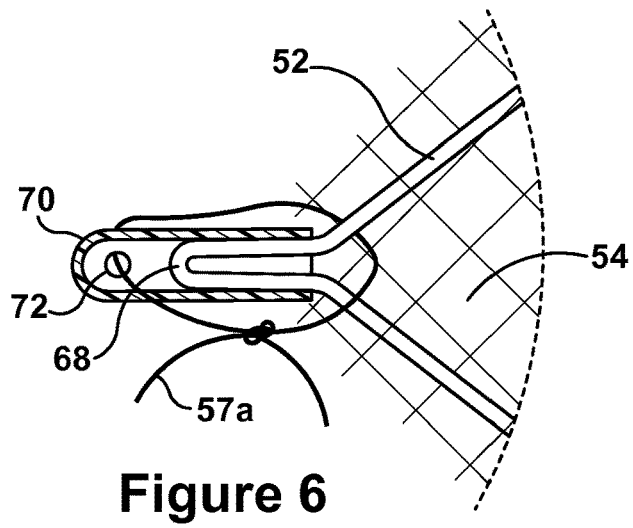
FIG. 6 is an exploded fragmentary view of the net of a retrieval device, showing yet another alternative distal end of the loop.

Referring to FIG. 6, an exploded fragmentary view of other alternative structure of the distal end of the loop 52 is shown. As in the embodiment shown in FIG. 5, the distal end of the loop 52 is bent into a protruding tip 68. Over the spring tip 68, a tip cap member 70 is press fit or connected by another suitable technique. The tip 70 may be constructed of plastic or any other suitable material. The tip 70 includes an aperture 72 therethrough as a distal end. As shown, the tether or anchor 57a is placed through the aperture and tied off to secure the net element 54 to the loop 52. To be discussed in greater detail, in one embodiment, a corresponding tether or anchor 57b can be used to secure the net element 54 on the proximal side of the retrieval net 50. The tether or anchor 57b is illustrated in FIGS. 14a-14b as a tie-off. It should be understood by those with ordinary skill in the art that the illustrated tethers or anchors 57a, 57b are for exemplary purposes only, and that other tether or anchor techniques and structure may be used in the practice of the invention.

Figure 10:
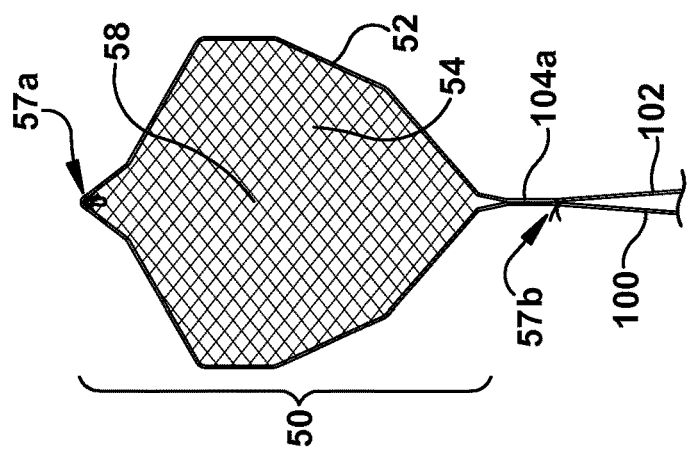
FIGS. 8-10 are views of a portion of the device of FIG. 4, showing the portion during a variety of assembly steps.
Figure 9:
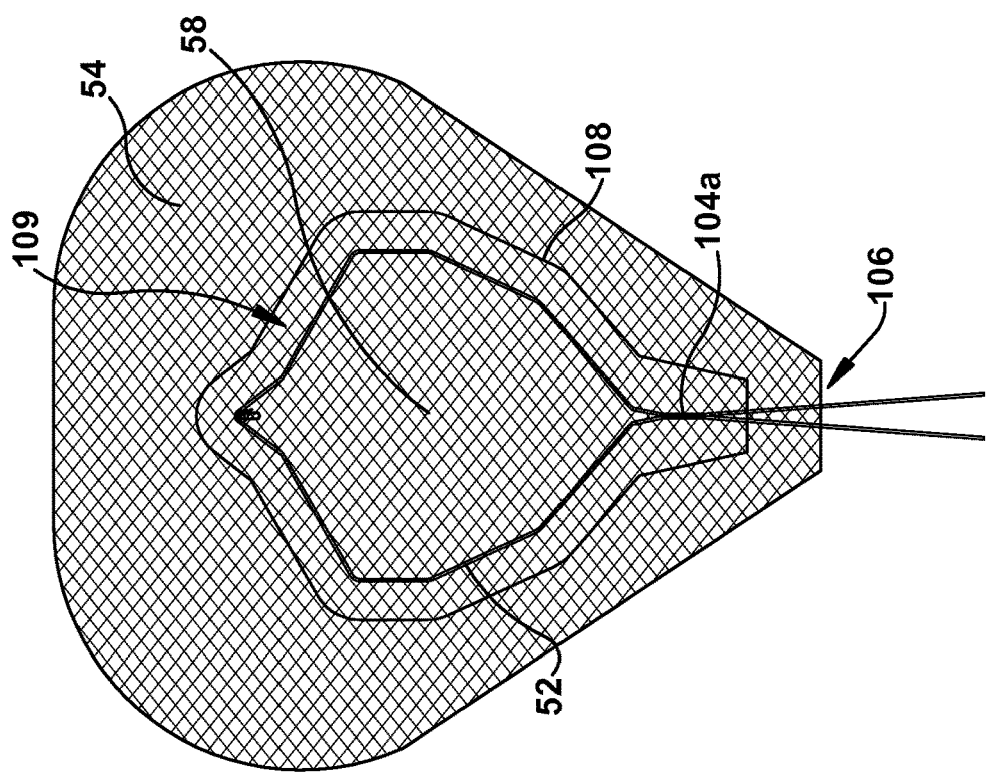
Figure 8:
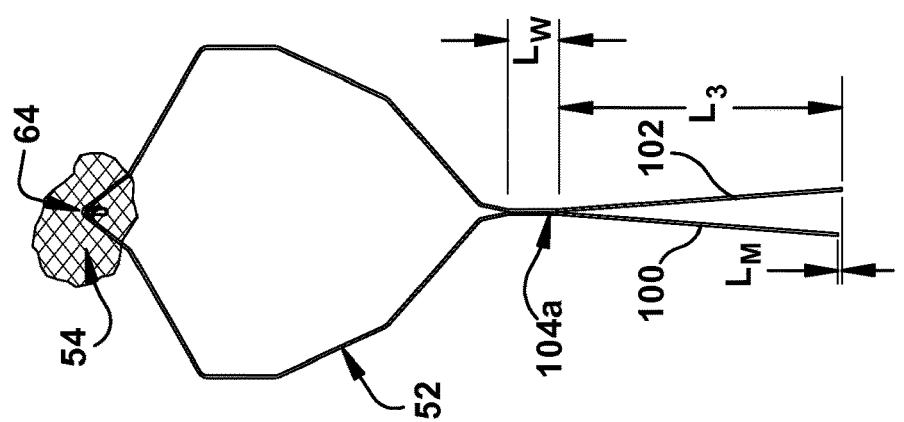

Referring now to FIGS. 8-10, a portion of the device of FIG. 4 is shown during a variety of assembly steps. The loop 52 of the wire is shown in FIG. 8 in a polygon form prior to assembly within the tube 24. The wire extends back toward the proximal end of the device 10 and forms two adjacent, or leg, portions 100 and 102. The leg portions 100, 102 are secured to each other by a connection 104a, such as for example, with a weld or by crimping or twisting the portions together, having an axial length $L_w$ of sufficient size to secure the portions together. As shown, the leg portions 100, 102 are joined by a weld 104a. The leg portions 100, 102 extend beyond the weld 104a a length $L_3$. The extension lengths of the two leg portions 100, 102 may be mismatched by a length $L_m$, but this mismatch is not required. The mismatch in extension lengths of the two leg portions 100, 102 allows space to connect the two leg portions to the cable during manufacturing of the device.

The net element 54 is shown in FIGS. 8-10 in various stages of assembly. In FIG. 8, the net element 54 is shown as it is just beginning to be woven around the flat wire loop 52. For purposes of perspective only, the net element 54 is shown in various positions in FIG. 9. With the net element 54 in a first position, the net element has an outer edge 106. In this first position, the net element 54 is shown to have the outer edge 106 cooperatively shaped with the loop 52. It should be apparent to others with ordinary skill in the art that a variety of net shapes and sizes can be utilized in the practice of this invention. The outer edge 106 illustrates the size of the net element 54 in relation to the loop 52 prior to the net element being woven on the loop.

In a second position, the outer edge of the net element 54 now becomes line or outer edge 108. The second position shows net element 54 after it is woven on the loop 52. As can be seen, after the net element 54 is woven on the loop 52, the outer edge 106 of the net element 54 is now closer in position to the loop 52. This change in position creates the receiving pouch 58. As shown in FIG. 9, the net element 54 in the second position or woven position includes an outer peripheral portion 109 that extends beyond the loop 52. As shown in FIG. 10, this excess portion 109 can be trimmed or otherwise removed prior to final assembly.

Two tethers or anchors are shown anchoring the net element 54 to the loop 52 in FIG. 10. A first distal tether or anchor 57a is shown, as previously described in regard to FIGS. 3 and 4. A second proximal tether or anchor 57b is shown and extends from the net element 54 to the proximal side of connection 104a securing the leg portions 100, 102 to each other. The second proximal tether or anchor 57b is shown in more detail in FIGS. 14a and 14b.

FIG. 11 is a front elevation view of the device shown after subsequent assembly steps have been completed. A second connection 104b proximal to the first connection 104a is shown. As shown, the second connection 104b is a weld. The second connection 104b joins the leg portions 100, 102 with a cable 110. As best shown in FIG. 12a, the leg portions 100, 102 are extended over the cable a length Lw. Also, as shown in FIG. 8, the leg portions 100, 102 may be mismatched. The size and length of the proximal connection 104b may be the same or different than the length of the distal connection 104a. The connection 104b is of adequate strength to maintain correlating axial movement between the cable 110 and the leg portions 100, 102. In FIG. 12b, a section of heat shrink material 112 is shown over the connection 104b to inhibit damage to the tubular member.

Referring now to FIG. 13, the proximal end of the cable 110 is anchored axially in relation to the handle by a length of hypodermic tube 114. In FIG. 13, the cable 110 is shown secured to the tube 114 by a swage connection 116 having a length $L_s$. The tube 114 extends distally beyond the swage connection 116 of length $L_5$. The swage connection 116 is of adequate strength to maintain correlating axial movement between the tube 114 and the cable 110. As shown in FIG. 11, the overall length of the motion transmitting link, which includes the tube 114 and the cable 110, is $L_4$.

FIG. 14a is an enlarged view of the distal portion 28 of the tube 24. As shown, the tether or anchor 57b anchors the proximal portion of the net element 54 and extends from the net element to the proximal side of the weld connection 104a. As shown, no internal connectors are used in this design to close the loop 52 or secure the loop 52 to the cable 110.

FIG. 14b is another enlarged view of the distal portion 28 of the tube 24. As shown, the ends of the leg portions 100, 102 of the wire are connected to the cable 110. However, the leg portions 100, 102 of the wire may be connected, or secured, to each other, such as for example, with a weld or by crimping or twisting the portions together, but is not shown. In FIG. 14b, the tether or anchor 57b anchors the proximal, or tail, portion of the net element 54 to a 360 curved portion 192 of leg portion 102 of the wire. It should be apparent to others with ordinary skill in the art that the curved portion may be included on either or both leg portions of the wire.

In the exemplary device shown in FIGS. 1-14b, the tube 114, cable 110, and connections thereof axially connect to form the transmitting link 34. However, other combinations of elements are possible.

A net element 254 is shown in FIG. 15 according to another embodiment of the invention. As shown, the net element 254 has an outer edge 206 cooperatively shaped with the loop portion 252 of the device 200 shown in FIG. 16. It should be apparent to others with ordinary skill in the art that a variety of net shapes and sizes can be utilized in the practice of this invention. The edge 206 is illustrated as the size of the net element 254 in relation to the loop 252 prior to the net element being woven on the loop. Further, as shown, the proximal portion of the net element 254 comprises a tail portion 290. As will be discussed, the tail portion 290 is used to secure the net element 254 to the wire.

Figure 17:
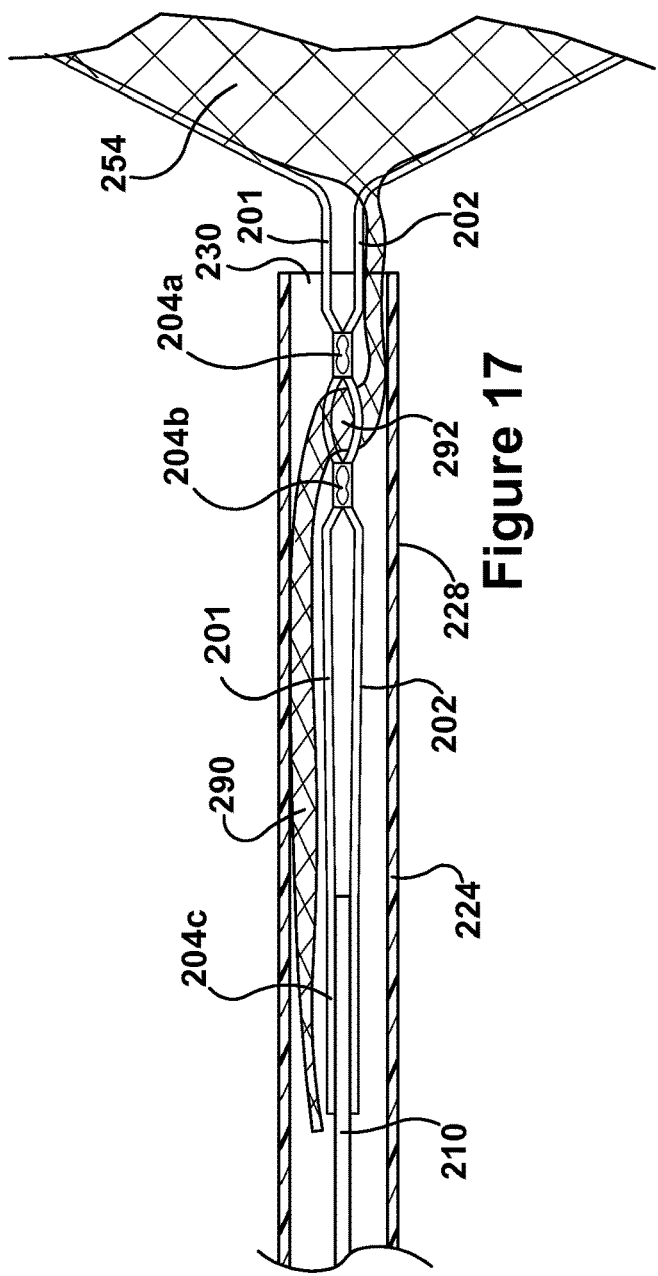
FIG. 17 is a cross-sectional fragmentary view of the distal portion of the device illustrated in FIG. 16, showing a retrieval net in a deployed position.
Figure 18:
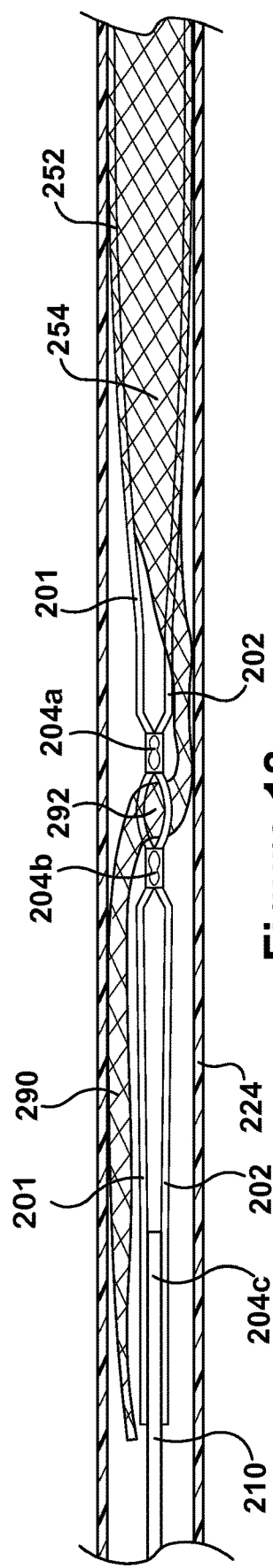
FIG. 18 is a cross-sectional fragmentary view of the distal portion of the device illustrated in FIG. 16, showing the retrieval net in a stored position.

FIGS. 16-18 show a device 200 according to another embodiment of the invention. As shown in FIG. 16, the device 200 includes a retrieval net 250. The retrieval net 250 includes a wire forming a loop portion 252 and two adjacent leg portions 201, 202 and a net element 254 secured to the loop portion. The net element 254 is supported by the loop portion 252 by threading, or weaving, the wire through holes in the net element. As shown in FIG. 16, a tether or anchor 257a disposed at the distal portion of the net element 254 anchors the net element to the loop portion 252 at a distal end of the loop portion.

The retrieval net 250 of device 200 is designed for movement between two positions. FIG. 16 shows the retrieval net 250 in a deployed position. FIGS. 17 and 18 are cross-sectional views of a distal portion of the device 200, showing the loop portion 252 of the retrieval net in a deployed position (FIG. 17) and stored position within the tube 224 (FIG. 18). As shown in FIG. 18, the retrieval net is disposed within the tube 224 for deployment and retrieval through the tubular member lumen opening. By movement of the handle 218 relative to the body 214, the retrieval net 250 is movable between either the deployed or stored positions.

Referring again to FIGS. 16 and 17, the retrieval net 250 is illustrated in a deployed position and fully expanded outside of the tube 224 second end 228. The net element 254 may be constructed of any suitable light weight material, such as for example, nylon mesh string. The net element 254 has a centrally located object receiving pouch section 258. Further, as shown, the proximal portion of the net element 254 includes a tail portion 290.

As shown in FIGS. 16-18, the wire extends back toward the proximal end of the device 200 and forms two adjacent leg portions 201 and 202. The leg portions 201, 202 are secured to each other by two connections 204a, 204b. As shown, the leg portions 201, 202 are joined by two welds. However, the leg portions 201, 202 may be secured to each other by any suitable method known in the art, such as for example by crimping or twisting the portions together.

As shown in FIGS. 16-18, the tail portion 290 of the net element 254 is routed between the connections 204a, 204b to secure the proximal portion of the net element to the wire. As such, the tail portion 290 of the net element 254 is secured, or pinched, within the opening 292 defined by the connections 204a, 204b and the two leg portions 201, 202. Securing the proximal portion of the net element 254 between the connections 204a, 204b reduces the cost and complexity of manufacturing the retrieval device. Further, no tether or anchor is used to secure the proximal portion of the net element, reducing the chance of the net element tearing at the tether connection point, or the tether or anchor itself ripping.

Further, as shown in FIGS. 17-18, the tail portion 290 of the net element 254 at least partially surrounds the connection 204c of the leg portions 201, 202 to the cable 210. The tail portion 290 of the net element 254 provides a damping effect on the cable 210 movement toward the distal end 228 of the tube 224 when the handle 218 is activated. This also provides more control over the deployment of the net and cable 210 and controls the portion of the device that exits the opening of the tubular member 224 when the retrieval net is in the deployed position. The mesh of the tail portion 290 of the net element 254 also helps to center the leg portions 201, 202 of the wire and the cable 210 within the tubular member 224. The mesh of the tail portion 290 of the net element 254 also inhibits damage to the connections 204a, 204b, and 204c and the inside of the tubular member 224.

In another embodiment of the invention, the net element has a distally protruding portion and a proximally protruding portion. The protruding portions are shaped and adapted to permit an operator at assemble and secure the net element directly to a corresponding segment of the wire without the use of a tether. The distally protruding portion is secured directly to a distal end of the loop portion. The proximally protruding portion is secured between the two leg portions at a location proximal from the second connection.

Figure 19:
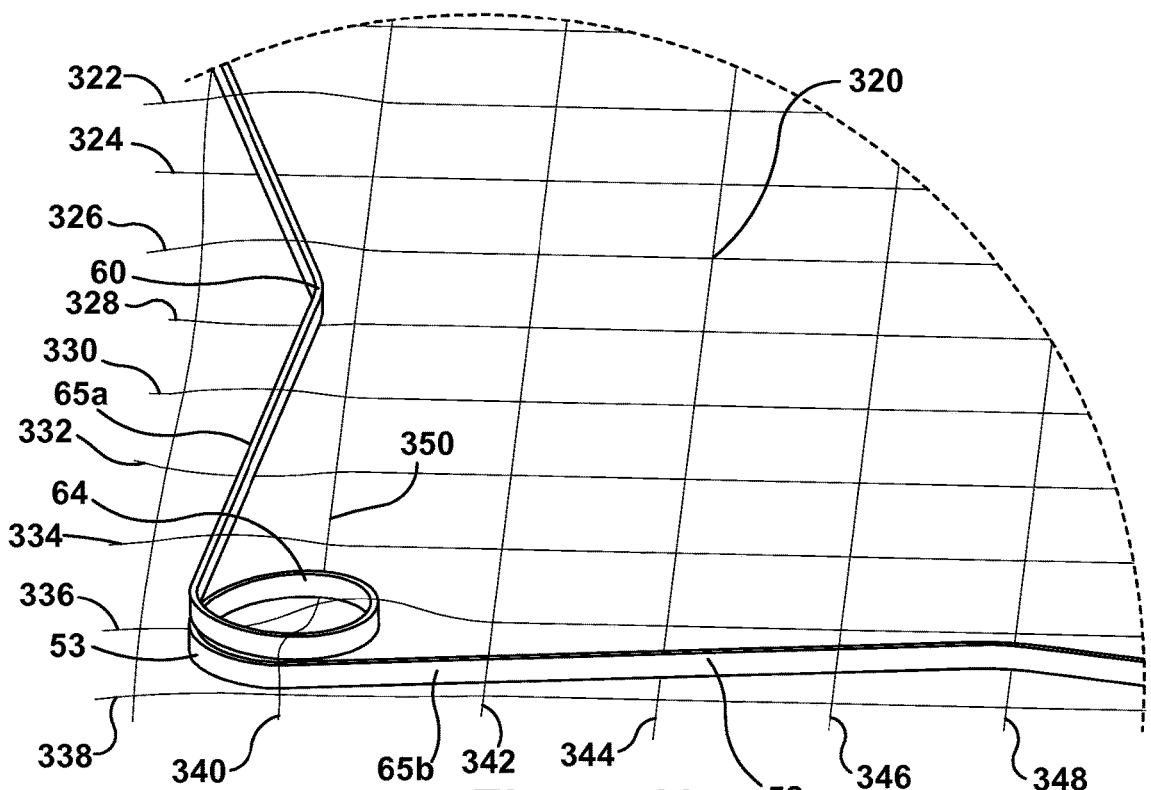
FIG. 19 is an exploded perspective view of a distal portion of a device, showing another embodiment of the invention with the net element attached directly to the distal end of the loop.

Referring now to FIG. 19, a perspective view of a distal portion of a retrieval device is shown. The net element 320 is attached directly to the distal end of the loop 52 without the use of a tether. The net element 320 is constructed from suitable light weight material, such as for example, a plurality of nylon mesh string, such as for example, the illustrated strings 322, 324, 326, 328, 330, 332, 334, 336, 338, 340, 342, 344, 346, 348 forming a woven pattern. At least some of the strings collectively form a distally protruding portion 350 of the net element 320.

The distally protruding portion 350 is connected directly to the distal end of the loop 52. In the illustrated example, the strings alternate in position, extending either above or below the polygon segments 65a, 65b. For example, illustrated string 340 is over an external portion of the curved portion 64 and below an internal portion of the curved portion 64, while illustrated 336 is under an external portion of the curved portion 64 and above an internal portion of the curved portion 64, with portions of several strings 340, 336 woven into and through a center opening within the 360 degree curved portion 64. As such, the distally protruding portion 350 is secured to a distal end of the loop 52 at the curved portion 64. It should be apparent to others with ordinary skill in the art that the string pattern of FIG. 19 is for example only, and other string patterns may be utilized in the practice of this invention.

Figure 20:
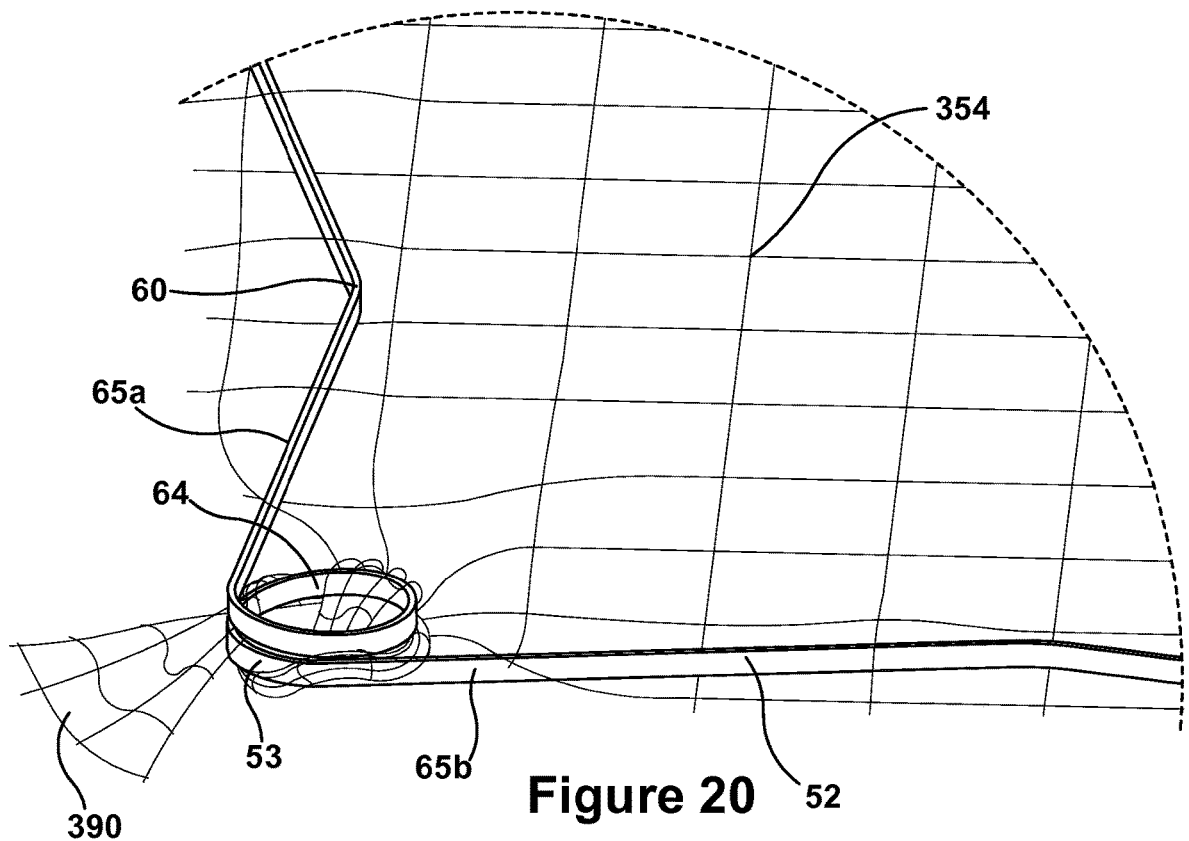
FIG. 20 is an exploded perspective view of a distal portion of a device, showing another embodiment of the invention with the net element attached directly to the distal end of the loop.

FIG. 20 shows another embodiment of the invention with the net element 354 attached directly to the distal end of the loop 52. The net element 354 includes a distally protruding portion 390. The protruding portion may be one of many shapes. The illustrated distally protruding portion 390 is in the shape of a tail. The tail is bundled and inserted through the curved portion 64 and secured to the curved portion by a knot. The tail may be secured by any function method or technique. The distal protruding portion 390 eliminates the need for a tether, tie or other securing element. As a result, assembly time, labor costs and material costs are reduced.

Specifically, FIG. 20 shows an example of a knot where the tail 390 is threaded top to bottom through an opening within curved portion 64, wrapped counterclockwise around a proximal exterior portion of curved portion 64, threaded between a top of the net element 354 and a bottom of polygon segment 65b, and pulled at least partially in between coils of the curved portion 64 to knot or secure the tail 390 to the curved portion 64 of the loop 52. It should be apparent to others with ordinary skill in the art that the tail routing pattern of FIG. 20 is for example only, and other tail routing patterns may be utilized in the practice of this invention.

Figure 21:
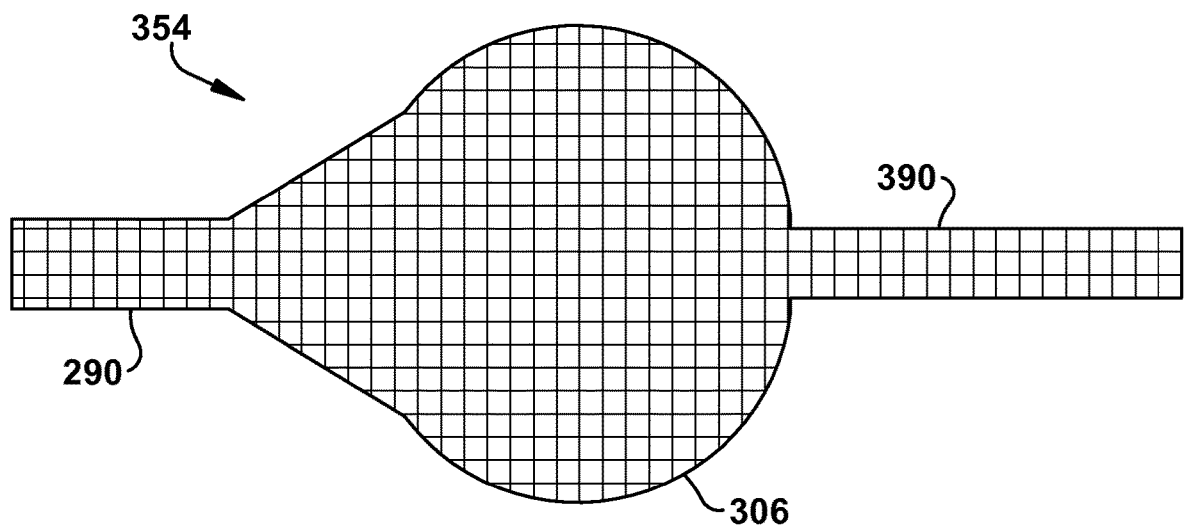
FIG. 21 is a top view of the net element of FIG. 20.

A top view of the net element 354 is illustrated in FIG. 21. As shown, the net element 354 has an outer edge 306 cooperatively shaped with the loop portion 252 of the device 200 shown in FIG. 16. It should be apparent to others with ordinary skill in the art that a variety of net shapes and sizes can be utilized in the practice of this invention.

The edge 306 is illustrated as the size of the net element 354 in relation to the loop 252 prior to the net element being woven on the loop. Further, as shown, the proximal portion of the net element 354 includes a tail portion 290. As discussed in regard to the device of FIG. 16, the tail portion 290 is used to secure the net element 254 to the wire. The distal portion of the net element includes a distally protruding portion. As shown, the distal portion includes a tail portion 390. As discussed, the tail portion is securable directly to a curved portion 64 without the use of a tether or other securing element.

In an exemplary operation using the device, the patient is intubated with an endoscope. The device 10 is inserted through an instrument channel of the endoscope, either before or after intubation. The device is inserted with the retrieval net in a stored position. The surgeon or operator utilizing the optical features of the endoscope will identify the object for removal. After identification of the object, the surgeon or operator will move the handle with respect to the base to deploy the retrieval net into the deployed position. The surgeon or operator will manipulate the object into the receiving pouch by one of a variety of techniques, including the use of additional endoscopic tools. For example, the surgeon or operator may manipulate the snare over the top of the object and enclose the net, or manipulate the snare under the object and enclose the net. Further, the surgeon or operator may use the net as a scoop, relying on the lateral stability of the device. Once the object is within the pouch, the surgeon or operator may manipulate the handle with respect to the body to slightly close the net around the object. FIG. 7 is a perspective view of a distal portion of the device illustrated in FIG. 4, showing a food bolus captured within the net. In this position, the loop retains an expanded configuration with an object 80 retained within the pouch section 58. The surgeon or operator may further close the loop to secure or hold the food bolus. The endoscope now may be removed from the patient with risk of loss of the food bolus greatly reduced as compared to prior art devices.

While several embodiments of the invention has been illustrated and described in considerable detail, the present invention is not to be considered limited to the precise construction disclosed. Various adaptations, modifications and uses of the invention may occur to those skilled in the arts to which the invention relates. It is the intention to cover all such adaptations, modifications and uses falling within the scope or spirit of the claims filed herewith.

We claim:

1. An endoscopic device for retrieving an object from within a human body, comprising:
   a support assembly including a base and an elongated tubular member;
   a transmitting assembly including a handle movable relative to the base, and a link having a first end fixed to the handle and a second end remote from the base, wherein the link extends through at least a portion of the tubular member;
   a wire defining a loop portion and two adjacent leg portions, wherein the loop portion begins and ends at a distal side of the two adjacent leg portions, such that each leg portion is disposed on a proximal side of the loop portion, wherein the two adjacent leg portions are secured to each other by a first connection at the distal side where the loop portion ends, wherein a length of each leg portion extending in a proximal direction from the first connection differs, wherein a proximal end of each leg portions is secured to the second end of the link by a second connection, and wherein portions of the two adjacent leg portions are not secured to each other between the second connection and the first connection; and
   a net element having a distal portion secured to the loop portion and a proximal portion, wherein the proximal portion includes a tail portion, wherein the net element has a mesh patterned structure, wherein a proximal portion of the mesh patterned structure extends at least to and directly contacts the two adjacent leg portions, wherein the proximal portion of the mesh patterned structure is directly secured to the two adjacent leg portions; wherein the tail portion at least partially surrounds at least one of the first connection and the second connection; and wherein the loop portion is movable between an expanded position outside the tubular member and a collapsed position within the tubular member by action of the handle relative to the base.

2. The device of claim 1, wherein the mesh patterned structure of the proximal portion is adhered to the two adjacent leg portions.

3. The device of claim 1, wherein the distal portion of the net element is adhered to the loop portion of the wire.

4. The device of claim 1 further comprising:
   a tether or anchor securing a proximal side of the net element at one or more of the two adjacent leg portions.

5. The device of claim 4, wherein the tether or anchor is secured to the proximal side of the net element and a curved portion of at least one of the two adjacent leg portions.

6. The device of claim 4, wherein the tether or anchor is secured between the two adjacent leg portions.

7. The device of claim 6, wherein the tether or anchor is secured between the two leg portions and between the first connection and the second connection.

8. The device of claim 1, wherein the tail portion surrounds both the first connection and the second connection.

9. The device of claim 1, wherein the tail portion only surrounds the first connection.

10. The device of claim 1, wherein the tail portion only surrounds the second connection.

\* \* \* \* \*